(12) United States Patent
Levy et al.

(10) Patent No.: US 6,332,888 B1
(45) Date of Patent: *Dec. 25, 2001

(54) FINGER-GUIDED SURGICAL INSTRUMENT

(75) Inventors: Gil Levy, Tel Aviv; Moshe Maroko, Hod Hasharon, both of (IL)

(73) Assignee: Urogyn Ltd., Ramat Gan (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/372,578

(22) Filed: Aug. 12, 1999

Related U.S. Application Data

(63) Continuation-in-part of application No. PCT/IL99/00084, filed on Feb. 9, 1999.

(30) Foreign Application Priority Data

Feb. 12, 1998 (IL) .................................................... 1232758

(51) Int. Cl.[7] .......................... A61B 17/062; A61B 17/28; A61B 17/32
(52) U.S. Cl. ........................... 606/144; 606/167; 606/174; 606/185; 606/205; 30/298; 294/25; 81/177.3
(58) Field of Search ................................ 606/1, 167, 205, 606/144, 147, 148, 174, 185, 222; 30/298; 294/25; 81/177.3

(56) References Cited

U.S. PATENT DOCUMENTS

| 310,108 | 12/1884 | Winzenried . |
|---|---|---|
| 622,386 | 4/1899 | Peery . |
| 1,040,761 | 10/1912 | Rives . |
| 2,025,357 | 12/1935 | Pagan . |
| 2,225,571 | 12/1940 | Smith . |
| 4,345,601 | 8/1982 | Fukuda . |
| 4,506,663 | 3/1985 | Baron . |
| 4,726,371 | 2/1988 | Gibbens . |
| 5,079,629 | 1/1992 | Oz . |
| 5,364,408 | 11/1994 | Gordon . |
| 5,423,795 | 6/1995 | Eckert et al. . |
| 5,458,609 | 10/1995 | Gordon et al. . |
| 5,540,704 | 7/1996 | Gordon et al. . |
| 5,575,800 | 11/1996 | Gordon . |
| 5,578,044 | 11/1996 | Gordon et al. . |
| 5,662,664 | 9/1997 | Gordon et al. . |
| 5,700,272 | 12/1997 | Gordon et al. . |
| 5,713,910 | 2/1998 | Gordon et al. . |
| 5,741,277 | 4/1998 | Gordon et al. . |
| 5,741,279 | 4/1998 | Gordon et al. . |
| 5,925,064 | 7/1999 | Meyers et al. . |
| 6,048,351 | 4/2000 | Gordon et al. . |

FOREIGN PATENT DOCUMENTS

| US97/11494 | 6/1997 | (WO) . |
|---|---|---|
| 98/00069 | 1/1998 | (WO) . |

OTHER PUBLICATIONS

Dainer et al, "The Burch Procedure: A Comprehensive Review", *CME Review Article,* 54(1):49–60, 1998.

Primary Examiner—Michael H. Thaler

(57) ABSTRACT

A finger-guided surgical instrument is described and includes (a) a thimble-like element being adapted to surround at least a portion of a surgeon's finger while at least partially exposing the ventral tactile portions of the distal phalanx thereof, so as to enable the surgeon to tactile sense a body location to be treated; (b) an ejectable surgical tool being engaged within a housing being formed within, or connected to, a wall of the thimble-like element; and (c) a mechanism for ejecting the surgical tool from the thimble-like element, so as to enable the surgeon to operate the body location.

17 Claims, 21 Drawing Sheets

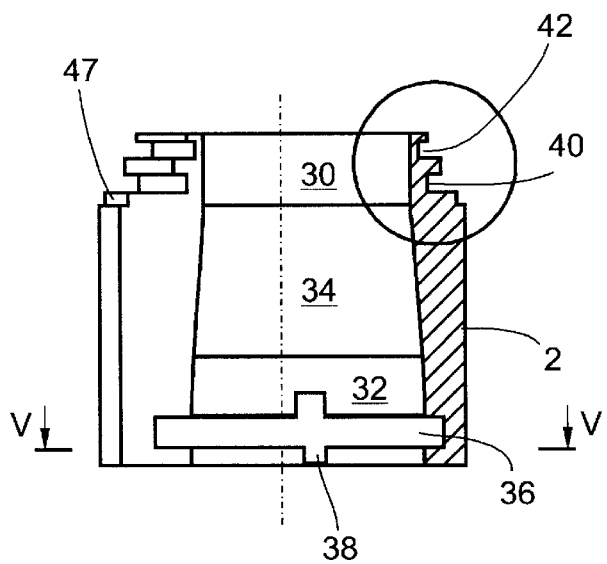
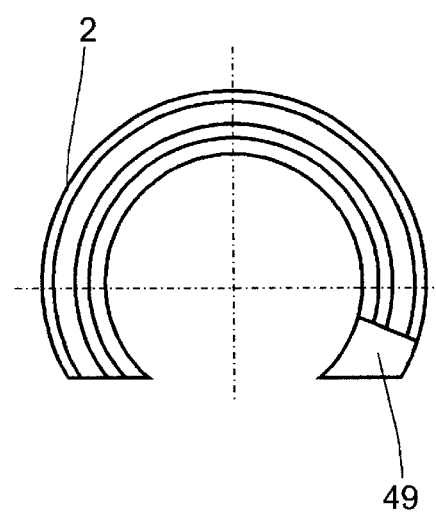
Fig. 3  Fig. 4
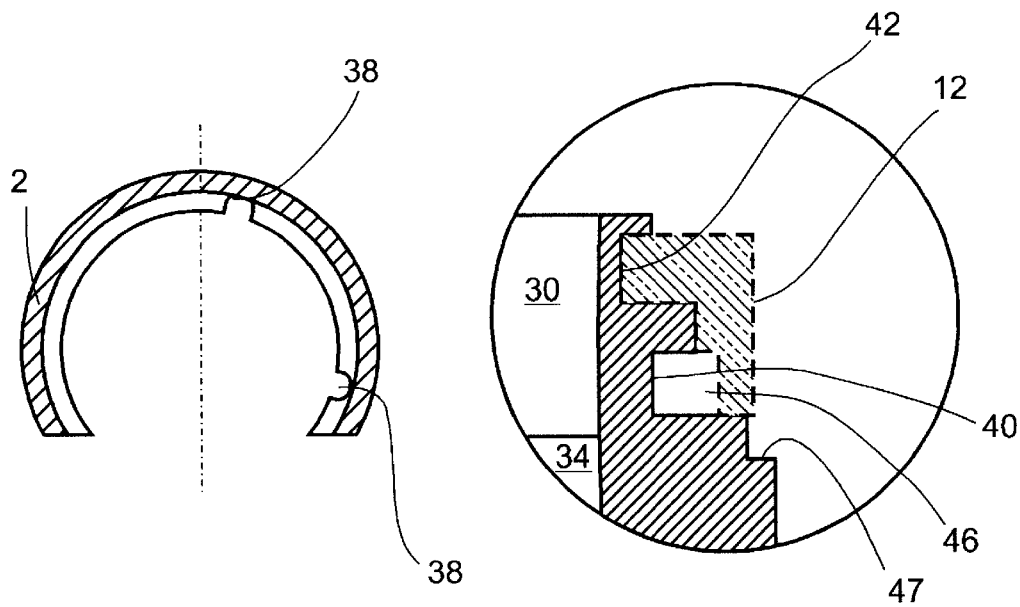
Fig. 5  Fig. 6

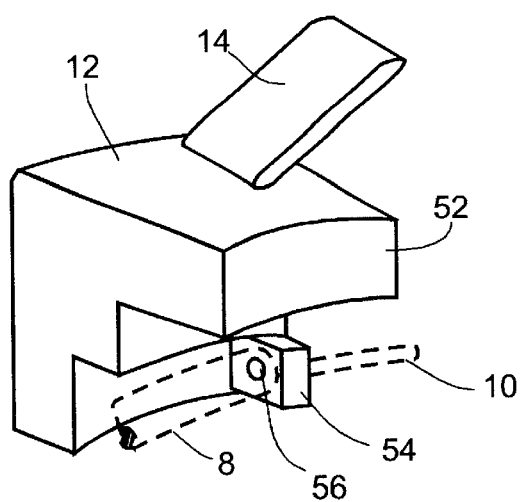
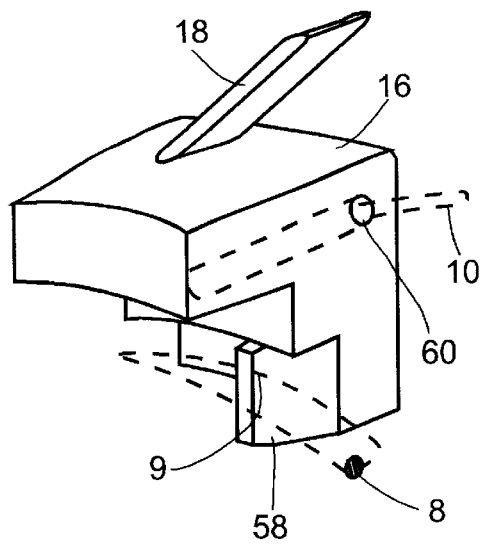
Fig. 12             Fig. 13
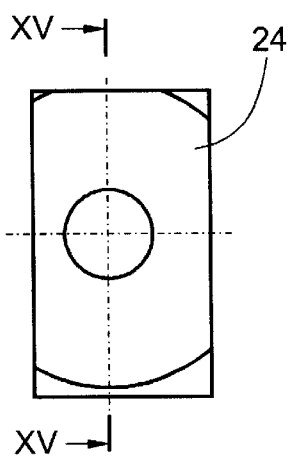
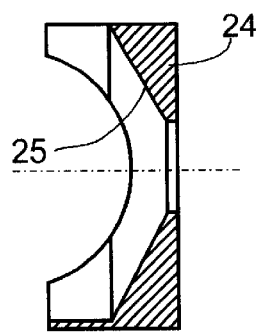
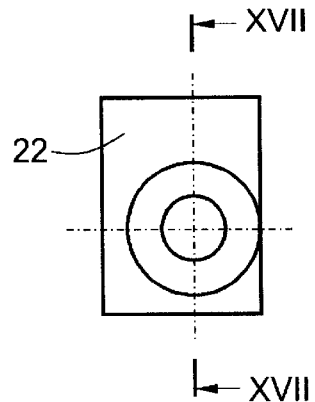
Fig. 14    Fig. 15    Fig. 16
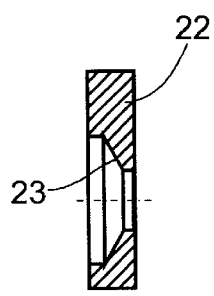
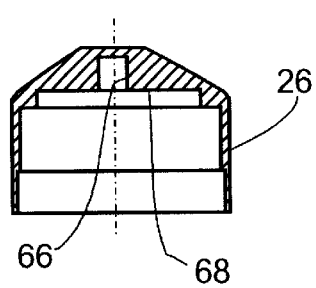
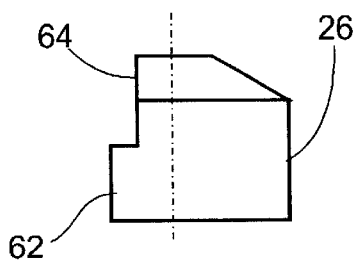
Fig. 17    Fig. 18    Fig. 19

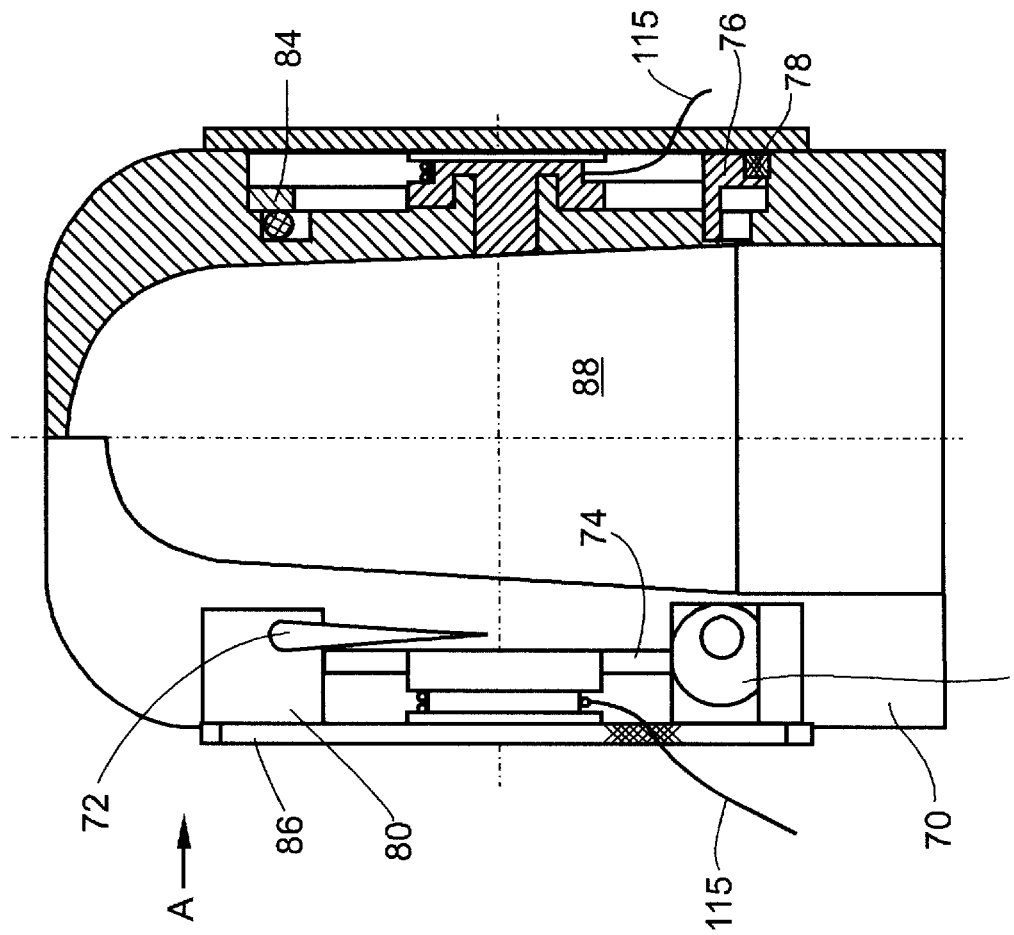
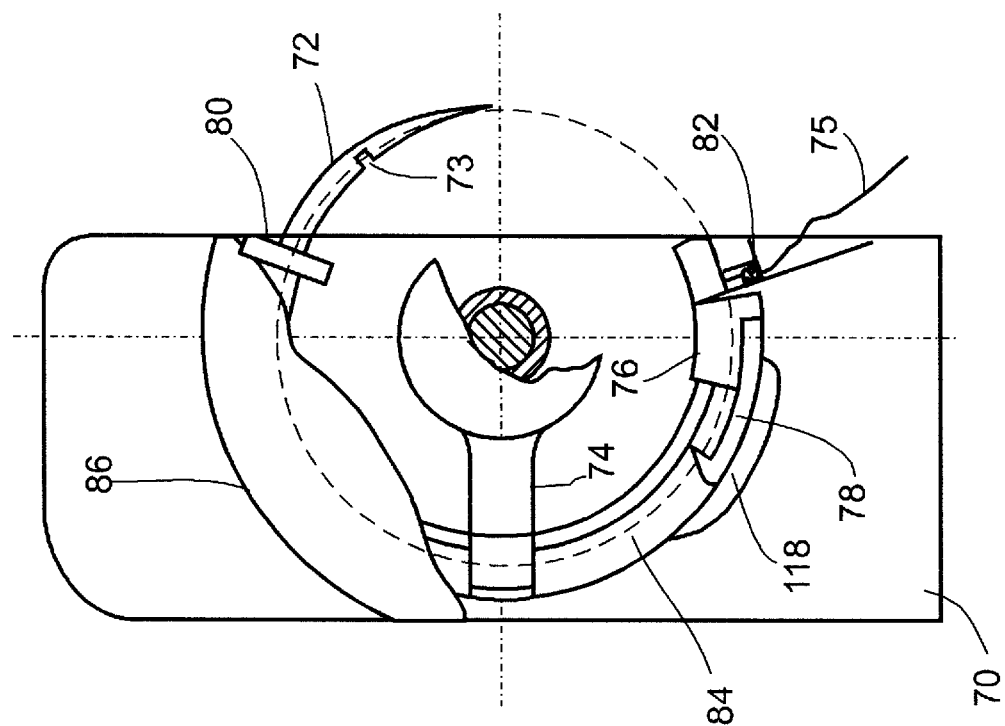

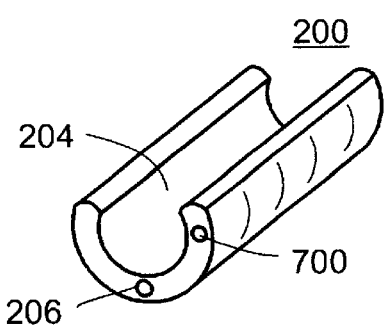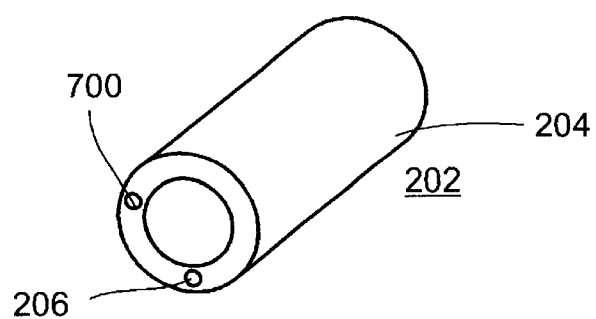
Fig. 34          Fig. 35
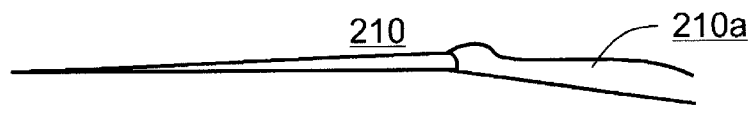
Fig. 36
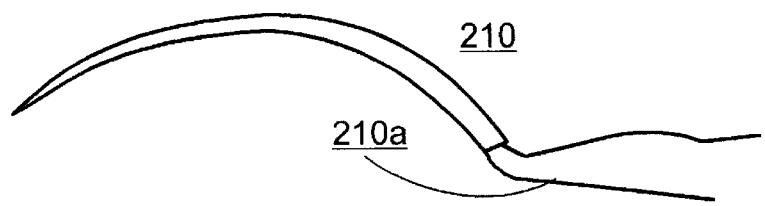
Fig. 37
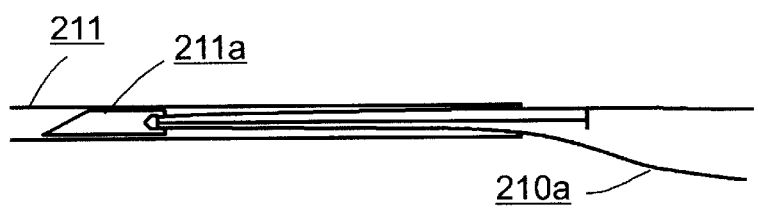
Fig. 38
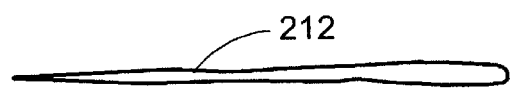
Fig. 39
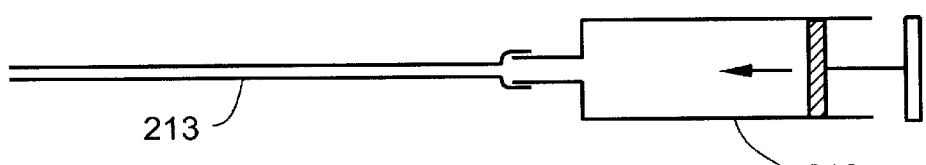
Fig. 40

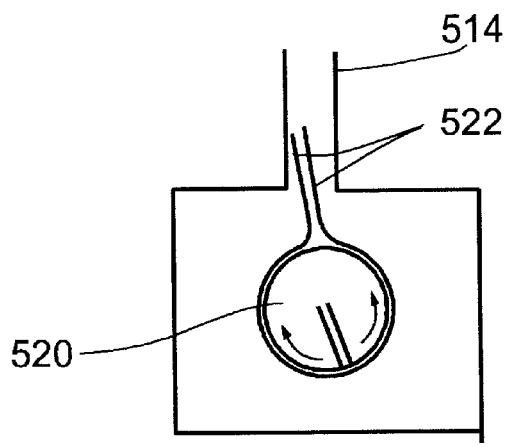
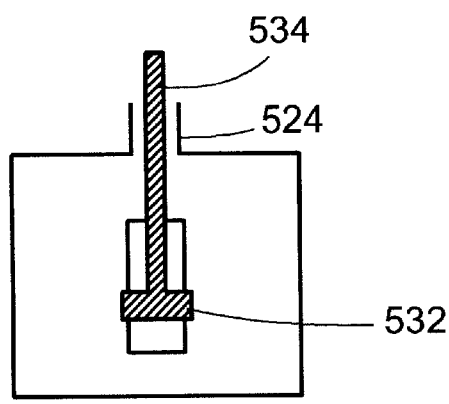
Fig. 70    Fig. 71
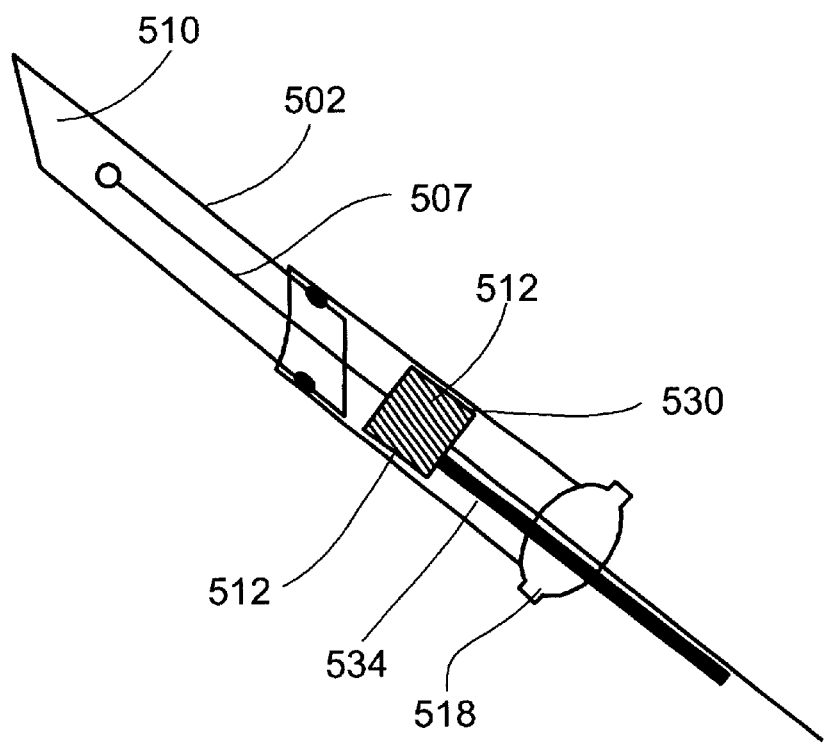
Fig. 72

FINGER-GUIDED SURGICAL INSTRUMENT

This is a continuation-in-part of PCT/IL99/00084 filed Feb. 9, 1999

FIELD AND BACKGROUND OF THE INVENTION

The present invention relates to surgical instruments, and more particularly, to finger-guided surgical instruments, for performing extra as well as intrabody surgical tasks, such as, but not limited to, cutting, grasping, suturing, sample collection by capillary forces or aspiration, placement of anchors and the like, especially in body locations of limited minimal-invasive accessibility. The present invention further relates to surgical procedures in which one or more finger-guided surgical instrument of the present invention are used to cut, grasp, suture, collect a sample, place anchors and the like, especially in body locations of limited minimal-invasive accessibility.

For years, there has been a discernible, clear tendency in surgery and invasive diagnosis, especially, but not exclusively, in abdominal, joint, vaginal, in-utero and brain, surgeries or diagnoses, to develop procedures that would reduce the need for major access-providing incisions with their concomitant requirements of general anesthesia, extended hospitalization and increased infection hazard. One step in this direction was the introduction of endoscopy and laparoscopy, which, through provision of minimal incision in, e.g., the abdominal wall of joint covering skin, permits the introduction into the abdominal cavity or joint of a miniature television camera including a light source, as well as of various surgical instruments.

PCT/U.S. Pat. No. 97/11494 teaches a number of surgical instruments which can be mounted directly on a surgeon's fingertips in a way that the surgeon can insert his or her hand into the patient through a minimal incision to perform surgical procedures, and also to use his or her fingers to manipulate tissues, thus enabling the surgeon to perform the procedures with the benefits of minimally invasive surgery, but with much greater tactile sense, control; and ease of manipulation. However, these surgical instruments (i) are carried by a finger and operated by the thumb, thereby are not applicable for procedures in which a single finger is employed for tactile sensing an operated intrabody location; (ii) include an operating head which permanently extends far beyond the fingertip on which the surgical instrument is mounted, which limits the tactile sensing of the surgeon; and/or (iii) prevent tactile sensing by the instrument carrying fingertip altogether.

Several surgical procedures are performed while the surgeon uses tactile information collected by a single fingertip for tactile sensing the intrabody site to be surgically operated prior to the actual surgical operation. Several non-limiting examples of such procedures are described in detail in the sections that follow. However, once the surgeon has collected the tactile information, surgical instruments are to be blindly operated intrabodily. Such instruments, in most part, engage both the hands of the surgeon. Evidently, blindly operating surgical instruments intrabodily based on finger tip tactile information collected earlier may prove inconvenient, inaccurate and may increase the chance of inadvertently harming the patient.

There is thus a widely recognized need for, and it would be highly advantageous to have, finger-guided surgical instruments devoid of the limitations associated with the prior art instruments and which enable a surgeon to use a single finger to both collect tactile information from an intrabody location to be surgically operated and to surgically operate that intrabody location with a finger-guided surgical instrument.

SUMMARY OF THE INVENTION

According to one aspect of the present invention there is provided a finger-mounted device for guiding a surgical instrument, the device comprising a thimble-like element being adapted to surround at least a portion of a surgeon's finger while at least partially exposing the ventral tactile portions of the distal phalanx thereof, so as to enable the surgeon to tactile sense a body location to be treated, the thimble-like element being formed with at lest one longitudinal guiding tunnel formed within a wall thereof, the at least one longitudinal guiding tunnel being for guiding the surgical instrument therethrough, so as to enable the surgeon to operate the body location.

According to another aspect of the present invention there is provided a finger-guided surgical instrument, comprising (a) a thimble-like element being adapted to surround at least a portion of a surgeon's finger while at least partially exposing the ventral tactile portions of the distal phalanx thereof, so as to enable the surgeon to tactile sense a body location to be treated; (b) an ejectable surgical tool being engaged within a housing being formed within, or connected to, a wall of the thimble-like element; and (c) a mechanism for ejecting the surgical tool from the thimble-like element, so as to enable the surgeon to operate the body location.

According to further features in preferred embodiments of the invention described below, the finger-mounted device for guiding a surgical instrument and/or the finger-guided surgical instrument of claim 1, further comprising an adapter insertable between the thimble-like element and the surgeon's finger, so as to adapt the guided surgical instrument to fingers of different size.

According to still further features in the described preferred embodiments the mechanism includes a first portion engaged within the housing and which is in contact with the ejectable surgical tool and a second, remote, portion extending out of the patient's body and which is operable by a free hand of the surgeon so as to eject the surgical tool from the thimble-like element.

According to still further features in the described preferred embodiments the mechanism includes a ratchet member disposed between the thimble-like element and the surgeon's finger so as to eject the surgical tool from the thimble-like element by twisting back and forth the surgeon's finger.

According to still further features in the described preferred embodiments the mechanism further serves for withdrawing the ejectable surgical tool back into the housing.

According to still further features in the described preferred embodiments the wall is a side wall of the thimble-like element.

According to still further features in the described preferred embodiments the wall is a front wall of the thimble-like element.

According to still further features in the described preferred embodiments the thimble-like element is constructed so as to be mounted over a dorsal side of the distal phalanx of the surgeon's finger, thereby exposing the entire ventral tactile portions of the distal phalanx. According to still further features in the described preferred embodiments the thimble-like element is constructed so as to fully surround the distal phalanx and expose the tip of the ventral tactile portion of the distal phalanx.

According to still further features in the described preferred embodiments the thimble-like element is constructed so as to be mounted over a ventral side of the distal phalanx of the surgeon's finger and expose the tip of the ventral tactile portion of the distal phalanx.

According to still further features in the described preferred embodiments the surgical tool is ejectable in a direction generally in extension of a longitudinal axis of the thimble like element.

According to still further features in the described preferred embodiments the surgical tool is ejectable in a circular path.

According to still further features in the described preferred embodiments the circular path on a plane which substantially parallels a plane traversing the surgeon's finger from top to bottom.

According to still further features in the described preferred embodiments the circular path on a plane which substantially parallels a plane traversing the surgeon's finger from side to side.

According to still further features in the described preferred embodiments the circular path on a plane which is substantially perpendicular to the longitudinal axis of the surgeon's finger.

According to still further features in the described preferred embodiments the surgical tool is selected from the group consisting of a surgical needle, a needle carrying a surgical anchor ejectable therefrom, a puncturing device, an injection needle, a capillary, a puncturing capillary, a miniaturized surgical grasper, miniaturized surgical scissors, a miniaturized blade and an aspiration capillary.

According to still further features in the described preferred embodiments the finger-mounted device for guiding a surgical instrument and/or the finger-guided surgical instrument, further comprising a reporting mechanism for reporting at least one situation selected from the group consisting of a full ejection of the surgical tool, a full withdrawal of the surgical tool, a degree of ejection of the surgical tool and a degree of withdrawal of the surgical tool.

According to yet another aspect of the present invention there is provided a finger-guided surgical instrument, comprising (a) a thimble-like element being adapted to surround a portion of a surgeon's finger while exposing the ventral tactile portions of the distal phalanx thereof, so as to enable the surgeon to tactile sense a body location to be treated; (b) an ejectable substantially semi-circular surgical needle being engaged within a housing being formed within, or connected to, a wall of the thimble-like element, the surgical needle being for holding and guiding a suture; and (c) a mechanism for ejecting the surgical needle in a circular path through an ejection opening in the housing from the thimble-like element and thereafter withdrawing the surgical needle back into the thimble-like element through a withdrawal opening in the housing, so as to enable the surgeon to suture the body location.

According to further features in preferred embodiments of the invention described below, the finger-guided surgical instrument further comprising a suture attached to one end thereof of the substantially semi-circular surgical needle.

According to still further features in the described preferred embodiments the mechanism includes a substantially semi-circular channel formed in the housing and connecting the ejection and withdrawal openings and which fully engages the substantially semi-circular surgical needle before its ejection and following its withdrawal, so as to direct the substantially semi-circular surgical needle in the circular path around a virtual axis, the mechanism further includes a remotely treated rotating arm being in the hosing and rotatable about a hinge, the rotating arm is designed to eject the substantially semi-circular surgical needle through the ejection opening by pushing a rear portion of the substantially semi-circular surgical needle and the rotating arm is further designed to withdraw the substantially semi-circular surgical needle through the withdrawal opening by pulling a front portion of the substantially semi-circular surgical needle.

According to still further features in the described preferred embodiments the virtual axis and the hinge are co-positioned.

According to still further features in the described preferred embodiments the virtual axis and the hinge are offset, whereas the rotating arm is an extendible-retractable arm.

According to still further features in the described preferred embodiments the substantially semi-circular surgical needle is formed with a notch at the front portion, the notch is designed to accept a distal end of the rotating arm.

According to still further features in the described preferred embodiments the substantially semi-circular surgical needle is formed with a notch at the rear portion, the notch is designed to accept a distal end of the rotating arm.

According to still further features in the described preferred embodiments the substantially semi-circular surgical needle is formed with a blunt rear end, the rear end is designed to be pushed by the rotating arm.

According to still further features in the described preferred embodiments the wall is a side wall of the thimble-like element.

According to still further features in the described preferred embodiments the wall is a front wall of the thimble-like element.

According to still further features in the described preferred embodiments the remotely treated rotating arm includes a rotating wheel portion rotatable about the hinge and an arm portion connected to, or integrally formed with, the rotating wheel portion, the mechanism further includes a remote rotation relay for relaying rotary motion from a remote rotatable actuator to the rotating wheel for effecting rotation of the rotating arm. According to still further features in the described preferred embodiments the finger-guided surgical instrument further comprising a flexible tube connecting between the housing and the remote rotatable actuator, the tube engaging the remote rotation relay.

According to still further features in the described preferred embodiments the thimble-like element is constructed so as to be mounted over a dorsal side of the distal phalanx of the surgeon's finger, thereby exposing the entire ventral tactile portions of the distal phalanx.

According to still further features in the described preferred embodiments the circular path on a plane which substantially parallels a plane traversing the surgeon's finger from top to bottom.

According to still further features in the described preferred embodiments the circular path on a plane which substantially parallels a plane traversing the surgeon's finger from side to side.

According to still further features in the described preferred embodiments the circular path on a plane which is substantially perpendicular to the longitudinal axis of the surgeon's finger.

According to still further features in the described preferred embodiments in the finger-guided surgical instrument further comprising a reporting mechanism for reporting at least one situation selected from the group consisting of a full ejection of the substantially semi-circular surgical needle, a full withdrawal of the substantially semi-circular surgical needle, a degree of ejection of the substantially semi-circular surgical needle and a degree of withdrawal of the substantially semi-circular surgical needle.

According to still another aspect of the present invention there is provided a finger-guided surgical instrument, comprising (a) a thimble-like element being adapted to surround at least a portion of a surgeon's finger while at least partially exposing the ventral tactile portions of the distal phalanx thereof, so as to enable the surgeon to tactile sense a body location to be treated; (b) an ejectable capillary being engaged within a housing being formed in a wall of the thimble-like element; and (c) a first mechanism for ejecting the ejectable capillary from the thimble-like element, so as to enable the surgeon to capillary sample the body location.

According to further features in preferred embodiments of the invention described below, the finger-guided surgical instrument further comprising (d) a translatably ejectable sleeve being engaged within the housing surrounding the ejectable capillary; and (e) a second mechanism for ejecting the translatably ejectable sleeve from the thimble-like element, so as to shield the body location from surrounding body fluids.

According to still further features in the described preferred embodiments the finger-guided surgical instrument further comprising (d) an ejectable puncturing device being engaged within the housing, the first mechanism further serves for ejecting the ejectable puncturing device from the thimble-like element, so as to enable the surgeon to wound the body location.

According to still further features in the described preferred embodiments the ejectable capillary has sharp edges so as to enable the surgeon to wound the body location.

According to still further features in the described preferred embodiments the ejectable capillary is a translatably ejectable capillary, whereas the first mechanism in a remotely treated translatable ejection mechanism.

According to still further features in the described preferred embodiments the ejectable capillary is a rotatably-translatably ejectable capillary, whereas the first mechanism is a rotatable-remotely treated translatable ejection mechanism.

According to still further features in the described preferred embodiments the ejectable capillary is an ejectable aspiration capillary, the finger-guided surgical instrument further comprising a remote aspirating device being in fluid communication with the ejectable aspiration capillary.

According to still further features in the described preferred embodiments the first mechanism further serves for withdrawing the ejectable capillary back into the housing.

According to still further features in the described preferred embodiments the wall is a back wall of the thimble-like element.

According to still further features in the described preferred embodiments the thimble-like element is constructed so as to be mounted over a ventral side of the distal phalanx of the surgeon's finger, thereby exposing the tip of the ventral tactile portion of the distal phalanx, underneath the nail. According to still further features in the described preferred embodiments the capillary is ejectable in a direction generally in extension of a longitudinal axis of the thimble like element.

According to still further features in the described preferred embodiments the finger-guided surgical instrument further comprising a reporting mechanism for reporting at least one situation selected from the group consisting of a full ejection of the capillary, a full withdrawal of the capillary, a degree of ejection of the capillary and a degree of withdrawal of the capillary.

According to still further features in the described preferred embodiments the finger-guided surgical instrument further comprising an optical head engaged by the thimble like element.

According to still further features in the described preferred embodiments the finger-guided surgical instrument further comprising a reporting mechanism in the capillary for reporting to the surgeon of at least one situation selected from the group consisting of a presence of fluid in the capillary and a level of fluid in the capillary.

According to an additional aspect of the present invention there is provided a finger-guided surgical instrument, comprising (a) a thimble-like element being adapted to surround at least a portion of a surgeon's finger while at least partially exposing the ventral tactile portions of the distal phalanx thereof, so as to enable the surgeon to tactile sense a body location to be treated; (b) at least one ejectable anchor guiding element being engaged within at least one housing being formed within, or connected to, at least one wall of the thimble-like element; (c) at least one first mechanism for ejecting the at least one anchor guiding element from the thimble-like element so, as to penetrate the body location; (d) at least one ejectable anchor being engaged within the at least one ejectable anchor guiding element; and (e) at least one second mechanism for ejecting the at least one ejectable anchor from within the at least one ejectable anchor guiding element, so as to enable the surgeon to anchor the at least one ejectable anchor in the body location.

According to further features in preferred embodiments of the invention described below, the finger-guided surgical instrument of claim 52, further comprising at least one cord attached to at least one anchor.

According to still further features in the described preferred embodiments the finger-guided surgical instrument further comprising at least one cord attached to the at least one anchor.

According to still further features in the described preferred embodiments the at least one cord is attached to the at least one anchor at a position so as to effect rotation and therefore efficient anchorage of the anchor when anchored in the body location by pulling on the cord.

According to still further features in the described preferred embodiments the at least one first mechanism includes at least one remotely treated rotating arm being in the hosing and rotatable about a hinge, the at least one remotely treated rotating arm is designed to eject the at least one ejectable anchor guiding element through at least one ejection opening in the at least one housing by pushing a rear portion of the at least one ejectable anchor guiding element, the at least one remotely treated rotating arm is further designed to withdraw the at least one ejectable anchor guiding element by pulling the rear portion of the at least one ejectable anchor guiding element in a reverse direction.

According to still further features in the described preferred embodiments the at least one second mechanism includes at least one remotely treated translatable ejection mechanism for ejecting the at least one anchor from the at least one ejectable anchor guiding element.

According to still further features in the described preferred embodiments the at least one wall is at least one side of the thimble-like element.

According to still further features in the described preferred embodiments the thimble-like element is constructed so as to be mounted over a dorsal side of the distal phalanx of the surgeon's finger, thereby exposing the entire ventral tactile portions of the distal phalanx.

According to still further features in the described preferred embodiments the finger-guided surgical instrument further comprising a reporting mechanism for reporting at least one situation selected from the group consisting of a full ejection of the at least one ejectable anchor, a full ejection of the at least one ejectable anchor guiding element, a full withdrawal of the at least one ejectable anchor guiding element, a degree of ejection of the at least one ejectable anchor guiding element and a degree of withdrawal of the at least one ejectable anchor guiding element.

According to still further features in the described preferred embodiments any of the above finger-mounted devices for guiding a surgical instrument and/or the finger-guided surgical instruments, further comprising an optical head engaged by the thimble like element.

According to yet an additional aspect of the present invention there is provided a finger-guided suturing device, comprising (a) a housing in the form of a body provided with a bore, the surface of which is substantially a surface of rotation, the housing being cut along a plane radially offset from an axial plane of the bore by such a distance as to cause the remaining bore to subtend an angle of more than 180°; (b) a thimble-like member adapted to partially surround, and fit with friction, a surgeon's finger while at least partially exposing the ventral portion of the distal phalanx thereof, the thimble-like member being movable within the housing with one degree of freedom in at least rotation; (c) a surgical needle of substantially semi-circular shape, one end of which constitutes the active point thereof and to the other end of which is fixedly attachable one end of a surgical suture, the needle being adapted to guidedly move in a first guide means of the housing end being further provided with a notch at a location close to the active point; (d) a ratchet member with arcuately arranged teeth, fixedly attached to, or integral with, the thimble-like member, (e) a needle pusher adapted to guidedly move in a second guide means of aid housing and being provided with an elastically deformable pawl member, whereby the needle pusher is mechanically coupled to the ratchet member when the latter rotates in one sense of rotation, and (f) a needle puller adapted to guidedly move in the second guide means of the housing and being provided with an elastically deformable pawl member, whereby the needle puller is mechanically coupled to the ratchet member when the latter rotates in the one sense of rotation, further comprising a tooth-like projection for engaging the notch in the needle to facilitate its pulling.

According to further features in preferred embodiments of the invention described below, the housing is substantially in the shape of a hollow cylinder, part of which has been cut away along a plane radially offset from an axial plane of the cylinder by such a distance as to cause the remaining cylindrical portion to subtend an angle of more than 180°.

According to still further features in the described preferred embodiments the first guide means is a first peripheral grove on the housing.

According to still further features in the described preferred embodiments the guide means is a second peripheral groove on the housing.

According to still further features in the described preferred embodiments the suturing device further comprising a cap contiguously mounted on, and substantially complementing the outer shape of, the housing, the cylindrical inside surface of the cap defining and delimiting the space inside which the needle pusher and the needle puller can move.

According to still further features in the described preferred embodiments the thimble-like member is provided with at least one projection matching a peripheral groove inside and housing, whereby the member is constrained to one degree of freedom in rotation only.

According to still further features in the described preferred embodiments, in addition to the peripheral inside groove, the housing is also provided with at least one axially directed inside groove, crossing and extending beyond the peripheral groove, whereby, in at least one angular position relative to the housing, the thimble-like member is also capable of a translational movement against the restoring force of a spring. According to still further features in the described preferred embodiments the suturing device, further comprising an exit guide for the needle, mounted at the location where the active point of the needle emerges from the device upon commencement of the suturing process.

According to still further features in the described preferred embodiments the suturing device further comprising an entrance guide mounted at the location where the active point of the needle re-enters the device at the conclusion of the suturing process.

According to still an additional aspect of the present invention there is provided a finger-guided suturing device, comprising a substantially prismatic housing having a bore, at least part of the length of which is tapering and adapted to partially surround and fit a surgeon's finger with friction while at least partly exposing the ventral portion of the distal phalanx thereof, the housing being cut along a plane distant from the axis of the bore so that the bore is exposed, but still surrounds the surgeon's finger over more than 180°, the device further comprising on each side of the prismatic housing (a) a recess having a central hole; and (b) two surgical needles of a substantially semi-circular shape, one end of each needle constituting the active point thereof and the other end thereof being fixedly attachable to one end of a surgical suture, the needles being adapted to guidedly move in a groove provided in the recess, each being further provided with a notch at a location close to the active point, and needle moving means rotatably mounted in each of the recesses and being rotatable in one sense of rotation by actuating first needle-manipulating means, and in the opposite sense of rotation by actuating second needle-manipulating means.

According to further features in preferred embodiments of the invention described below, the needle-manipulating means are cord means actuated by pulling.

According to still further features in the described preferred embodiments the needle moving means comprises needle pusher means advanced by pulling the first cord means and reversed by pulling the second cord means, the needle puller means adapted to guidedly move in the housing recesses, each comprising catch means for engaging the notch in the needle, as well as pawl means fixedly connected to or integral with the needle puller means, to engage the needle pusher means to effect the return of the needles into the housing.

According to still further features in the described preferred embodiments the needle pusher means and the needle puller means are one and the same component.

According to still further features in the described preferred embodiments the pawl means is fixedly connected to or integrated with the needle pusher means.

According to still further features in the described preferred embodiments the needle drivers are each provided with drum means, the first cord means being wound on each of the drums in one sense of winding, and the second cord means being wound on each of the drums in the opposite sense of winding.

According to still further features in the described preferred embodiments the catch means in the form of the tooth-like projection.

According to another aspect of the present invention there is provided a surgical procedure for bladder-neck suspension for treatment of urinary incontinence, the procedure comprising the step of suspending a pelvic fascia and a vaginal wall lateral to a urethra of a patient to Cooper's ligament by sutures being placed using a finger-guided surgical instrument having an ejectable, substantially semi-circular needle.

According to yet another aspect of the present invention there is provided a surgical procedure for treatment of recurrent shoulder dislocations, the procedure comprising the step of anchoring at least one anchor holding a cord to a glenoid rim of a patient and engaging a torn anterior-inferior or anterior-medial labrium thereto using the cord, wherein the at least one anchor is anchored in the glenoid rim via an anchor implanting device having at least one ejectable anchor guiding element engaging at least one ejectable anchor therein.

According to still another aspect of the present invention there is provided a surgical procedure for sampling blood from a fetus scalp during labor, the procedure comprising the step of sampling the blood into an ejectable capillary of a finger guided capillary device.

According to an additional aspect of the present invention there is provided a surgical procedure for treatment of rectal prolaps, the procedure comprising the step of constricting an anal opening by sutures being applied by using a finger-guided surgical instrument having an ejectable, substantially semi-circular needle.

According to yet an additional aspect of the present invention there is provided a surgical procedure for treatment of esophageal reflux, the procedure comprising the step of positioning a vessel loop around a esophagus of a patient using a finger-guided surgical instrument having an ejectable, substantially semi-circular needle.

According to still an additional aspect of the present invention there is provided a surgical procedure for treatment of vaginal prolapse, the procedure comprising the step of tying an upper part of a vagina of a patient to a sacrospinous ligament of the patient by sutures being placed using a finger-guided surgical instrument having an ejectable, substantially semi-circular needle.

According to a further aspect of the present invention there is provided a surgical procedure for treatment of rupture of a rectum in large animals, the procedure comprising the step of suturing the rapture using a finger-guided surgical instrument having an ejectable, substantially semi-circular needle.

According to yet a further aspect of the present invention there is provided a surgical procedure for treatment of rupture of a cervix in large animals, the procedure comprising the step of suturing the rapture using a finger-guided surgical instrument having an ejectable, substantially semi-circular needle.

According to still a further aspect of the present invention there is provided a surgical procedure for treatment of rupture of a uterus in large animals, the procedure comprising the step of suturing the rapture using a finger-guided surgical instrument having an ejectable, substantially semi-circular needle.

The present invention successfully addresses the shortcomings of the presently known configurations by providing finger guided surgical instruments having ejectable surgical tools and finger mounted devices for guiding surgical instruments, which maintains the user finger's ability for palpation.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the drawings:

FIG. 3 is a front view, in partial cross-section, of the housing of the needle driver;

FIG. 4 is a top view of the housing;

FIG. 5 is a view in cross-section along plane V—V in FIG. 3;

FIG. 6 represents an enlarge detail of the area encircled in FIG. 3;

FIG. 12 is a greatly enlarged, perspective view of the needle pusher of the invention;

FIG. 13 is a similar view of the needle puller;

FIGS. 14 and 15 are a front view and a side view in cross-section, respectively, of the entrance guide;

FIGS. 16 and 17 are similar views of the exit guide;

FIGS. 18 and 19 are a front view in cross-section and a side view, respectively, of the needle driver cap;

FIG. 20 is a partially cross-sectional front view of a dual needle driver according to the present invention;

FIG. 21 is a side view of the needle driver of FIG. 20 in the direction of arrow A;

FIGS. 34 and 35 are perspective views of finger-mounted devices for guiding a surgical instrument according to the present invention;

FIGS. 36–46 are cross sectional views of surgical instruments which can be guided using the finger-mounted devices of FIGS. 34–35, including a surgical needle, a needle carrying a surgical anchor ejectable therefrom, a puncturing device, an injection needle, a capillary, a puncturing capillary, a miniaturized surgical grasper, a miniaturized aspiration capillary, miniaturized surgical scissors and a miniaturized blade;

FIG. 70 is a cross sectional view of a remote rotating actuator employed in the device of FIG. 68;

FIG. 71 is a cross sectional view of a remote translating actuator employed in the device of FIG. 68;

FIG. 72 is a cross sectional view of an anchor guiding element and an anchor guided thereby of the device of FIG. 68;

DESCRIPTION OF THE PREFERRED EMBODIMENTS

Figure 1:
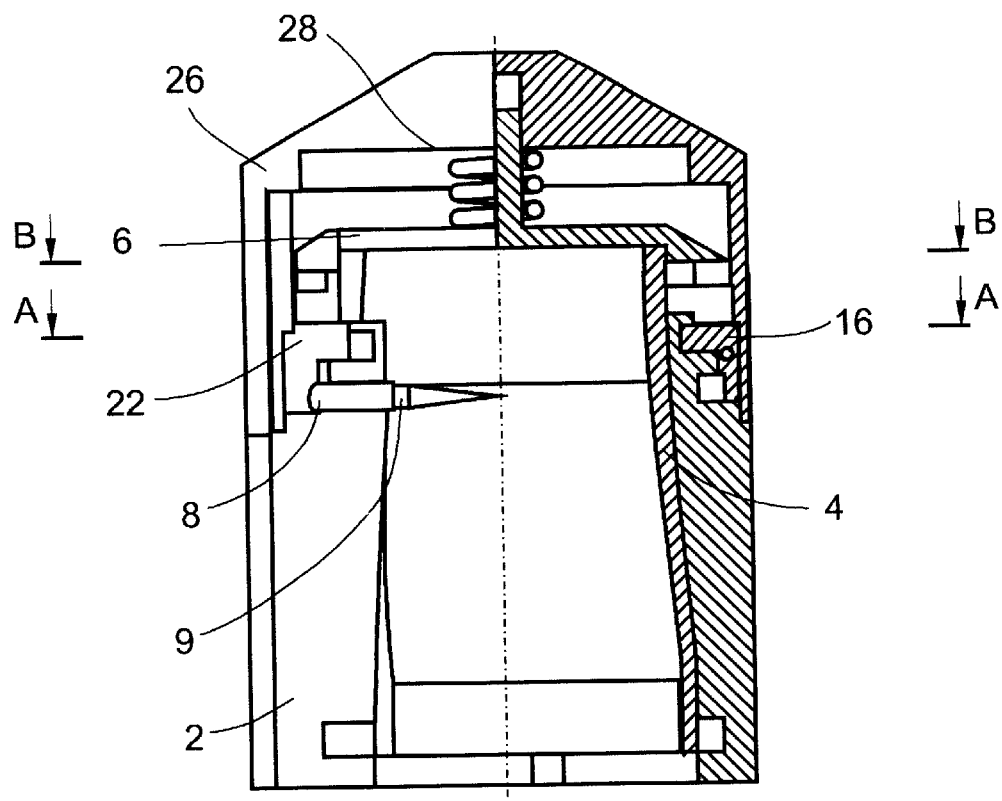
FIG. 1 is a front view, in partial cross-section, of a first embodiment of the needle driver according to the present invention.

The present invention is of finger-guided surgical instruments which can be used to perform extra as well as intrabody surgical tasks, such as, but not limited to, cutting, grasping, suturing, sample collection by capillary forces or aspiration, placement of anchors and the like. Specifically, the present invention can be used to perform surgical tasks in body locations of limited minimal-invasive accessibility. The present invention is further of surgical procedures in which one or more finger-guided surgical instrument of the present invention are used to cut, grasp, suture, collect a sample, place anchors and the like, especially in body locations of limited minimal-invasive accessibility.

The principles and operation of the instruments and procedures of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2:
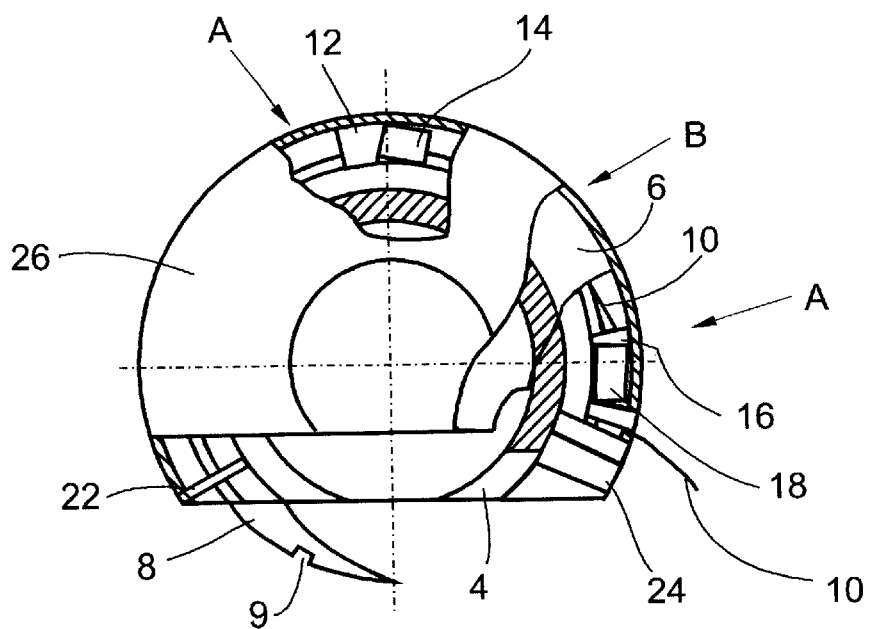
FIG. 2 is a top view, in partial cross-section, of the needle driver of FIG. 1.

Referring now to the drawings, FIGS. 1–33 relate to a finger-guided suturing device according to one aspect of the present invention. FIGS. 1 and 2 show a frontal view and a top view, respectively, of a first embodiment of this aspect of the present invention. These assembly drawings are intended to show the relative positions of the different components of the device, while the components themselves are illustrated in Figures of their own, as further detailed in the following sections.

It should be noted that the cross-sectional portions of FIG. 2 are not located in a common plane. Portions A are produced by cross-section along plane A—A in FIG. 1, while portion B is produced by cross-section along plane B—B in FIG. 1.

The first embodiment of the finger-guided suturing device according to the present invention comprises a housing 2, a thimble-like finger grip 4 rotatably fitting the inside of housing 2, an arcuate ratchet 6 fixedly attached to thimble-like finger grip 4, a substantially semi-circular surgical needle 8, to the rear end of which is fixedly attached a length of suture 10, a needle pusher 12 having a pawl 14 adapted to interact with ratchet 6, a needle puller 16 having a pawl 18 adapted to interact with ratchet 6, a needle catch 20 cooperating with needle puller 16, a needle exit guide 22, a needle entrance guide 24, a cap 26 and a helical spring 28.

Seen in FIGS. 3–5 is housing 2, which geometrically is substantially in the shape of a hollow cylinder, part of which has been cut away along a plane substantially parallel to, but radially offset from, an axial plane of the cylinder, as is clearly shown in FIG. 4. The hollow section thus subtends an angle larger than 180°.

The bore of housing 2 is seen to have three sections: an upper, cylindrical section 30, a lower, cylindrical section 32, and a tapering, intermediate section 34 connecting the two cylindrical sections. Further shown is an internal, peripheral groove 36 located near the lower end of housing 2 and serving to guidingly accommodate two lugs integral with finger grip 4 (FIG. 7) and permitting the latter one degree of freedom in rotation. Two further grooves 38 (of which only one is shown in FIG. 3) cut across grooves 36 and extend beyond them, facilitating the introduction of finger grip 4 upon assembling the device and also serve a further purpose, to be explained further below. The location of grooves 38 can be seen in FIG. 5.

Near the upper end of housing 2, there are shown a first peripheral groove 40 and, somewhat above it, a second peripheral groove 42. Groove 40, as will be explained further below in greater detail, accommodates substantially semi-circular surgical needle 8; groove 42 serves to guide two further components in their movement: needle pusher 12 and needle puller 16.

The enlarged detail of FIG. 6 shows groove 40 and groove 42 of housing 2, as well as ghosted-in needle driver 12 which, together with groove 40, defines a duct 46 which guides needle 8 (FIGS. 1 and 2) during the surgical procedure. Shoulder 47 (FIGS. 3 and 6) serves as abutment for cap 26 (FIG. 18).

In FIG. 4, there is shown an area 49 which has been cleared of the collar comprising grooves 40, 42 down to shoulder 47, to provide space for entrance guide 24 (FIGS. 14 and 15).

Figure 7:
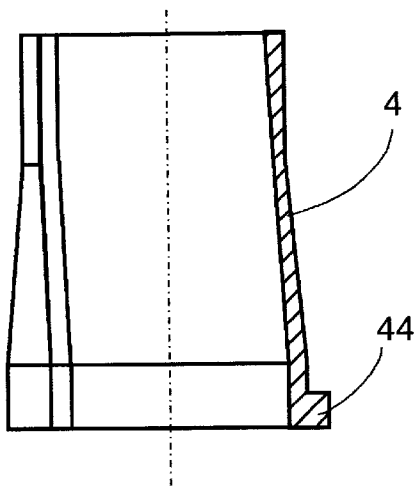
FIGS. 7, 8 and 9 represent partially cross-sectional front, top and side views, respectively, of the thimble-like grip.
Figure 8:
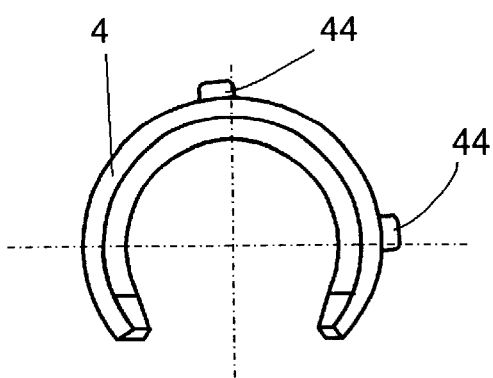
Figure 9:
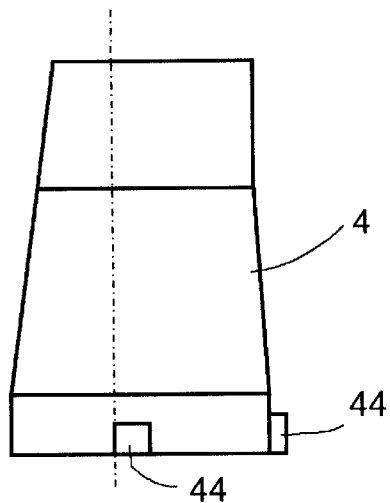

Represented in FIGS. 7 to 9 is finger grip 4, i.e., the thimble-like, cut-open sleeve located inside housing 2 that accommodates and grips the distal phalanx of the surgeon's index finger, leaving its ventral portion at least partly exposed for palpation. Also shown are two lugs 44 which, as mentioned above, are seated inside groove 36 in housing 2 and restrain the finger-imparted movement of finger grip 4 to rotary movement only, except when lugs 44 are brought into alignment with grooves 38 of housing 2 (FIG. 5), in which situation finger grip 4 is also capable of a short axial movement relative to housing 2, for a purpose to be explained further below.

Figure 10:
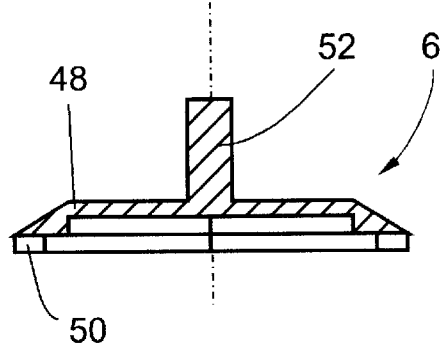
FIGS. 10 and 11 show a front view in cross-section, and a bottom view, respectively, of the ratchet of the needle driver.
Figure 11:
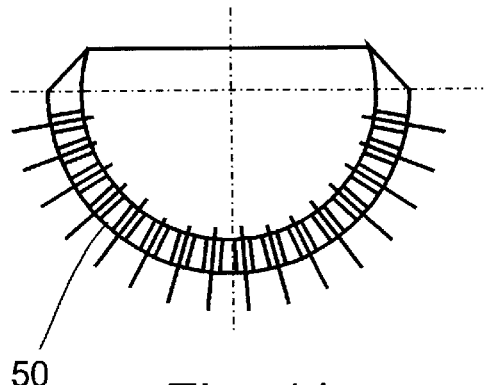
Figure 23:
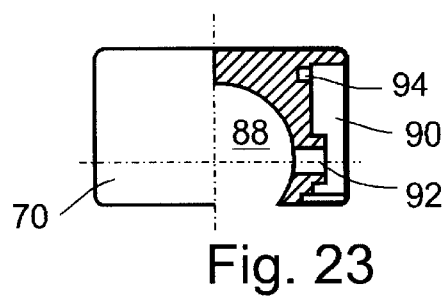
FIG. 23 is a partially cross-sectional top view of the housing.
Figure 22:
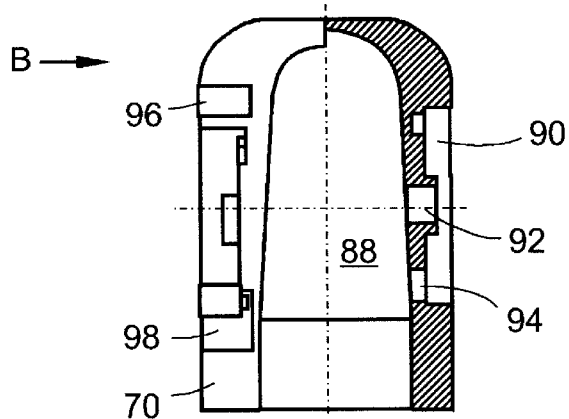
FIG. 22 is a partially cross-sectional front view of the housing of the needle driver of FIGS. 20 and 21.
Figure 24:
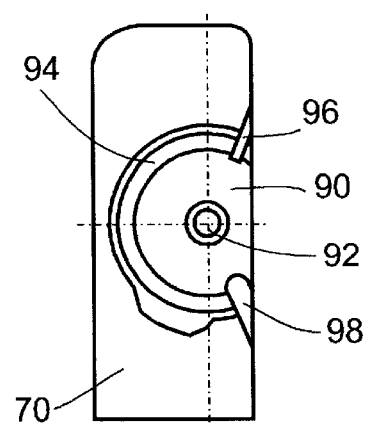
FIG. 24 is a side view of the housing in the direction of arrow B.

FIGS. 10 and 11 represent a ratchet 6 fixedly attached to, or integral with, finger grip 4. The purpose of ratchet 6 is to convert the reciprocative rotational motion of the surgeon's finger into an intermittent, unidirectional advance of surgical needle 8 (FIGS. 1 and 2). Ratchet 6 is seen to consist of a body 48, which carries on its underside an arcuate arrangement of ratchet teeth 50 subtending an angle of about 180°, and on its upper side, a rod 52, the purpose of which will become apparent further below.

Surgical needle 8 is of a substantially semi-circular shape and, near its sharp point, is provided with a notch 9 that is instrumental in returning needle 8 into housing 2 after completion of the stitch. The other end of needle 6 is provided with a bore, to which is attached a length of suture material 10.

FIG. 12 represents needle pusher 12, a nose 52 of which moves along and is guided by groove 42, as is clearly shown in FIG. 6. Pushing projection 54 moves in duct 46 (FIG. 6) and is seen to engage the rear end of needle 8, the suture passing through hole 56. In assembly, the elastically resilient pawl 14 is pressed against teeth 50 of ratchet 6. When the surgeon rotates his finger in the counter-clockwise direction, one of the ratchet teeth 50 engages pawl 14, whereby needle 8 is pushed along by pawl 14, needle pusher 12 and projection 54. The angular range over which the surgeon can twist his finger is of course limited (30–40°). At the end of the rotary motion, the finger returns in the clockwise direction to its original position. During this return movement, ratchet teeth 50 disengage from pawl 14 due to the slant of the latter, and needle pusher 12 remains stationary, in spite of the rotary movement of finger grip 4, and is again moved only when the surgeon's finger renews its "working stroke" in the counter-clockwise direction.

FIG. 13 represents needle puller 16 and its pawl 18. Needle puller 16 is quite similar to pusher 12, except that projection 54 is replaced by a catch 58 which, as can be seen in FIG. 13, fits notch 9 in ghosted-in needle 8. Also seen is a slanting hole 60, through which suture 10, coming from the rear of needle 8, leaves the suturing device.

From the moment needle 8 emerges from housing 2 via exit guide 22 and its flaring guide surface 23 (FIGS. 2, 16, 17), completes the stitching operation and fully returns into housing 2 via entrance guide 24 and its flaring guide surface 25 (FIGS. 2, 14, 15), needle movement is divided between needle pusher 12 and needle puller 16. At the beginning of the stitching procedure, needle puller 16 is located close to entrance guide 24 (FIG. 2), its pawl 18 being beyond the reach of ratchet teeth 50 (which extend only over an angular range of 180°). Needle pusher 12, on the other hand, is located well within the effective range of ratchet teeth 50 adjacent to the rear end of needle 9, and, thus, with each movement of the surgeon's finger, will advance needle 8 until the latter will reenter housing 2 via entrance guide 24. An additional movement of needle pusher 12 will have the following results: (i) catch 58 of needle puller 16 will engage in notch 9 of needle 8; and (ii) further movement of needle 8 by needle pusher 12 will drag needle puller 16, by means of catch 9, into the effective zone of ratchet teeth 50 and, at the same time, move itself beyond the reach of ratchet teeth 50.

Any further maneuver of the surgeon's finger will thus act on needle puller 16 and draw needle 8 fully back into housing 2. When this has been accomplished, the stitch has been completed and the finger, as well as the needle driver, can be withdrawn, leaving the suture material anchored in the tissue and permitting the surgeon to tie up the stitch.

It will be appreciated that exit guide 22 and entrance guide 24 could also be integral parts of housing 2.

FIGS. 18 and 19 represent cap 26 (FIG. 1) which, as mentioned above, is seated against shoulder 47 (FIG. 6) and defines and delimits the annular space in which needle pusher 12 and needle puller 16 move. Cap 26 is cut open along a plane 62, common with housing 2. A further cutting plane 64 is set back relative to plane 62. A bore 66 is a sliding fit to rod 52 of ratchet 6. As shown in FIG. 1, a helical compression spring 28 is mounted on rod 52 and, abutting against ceiling 68 of cap 26, pushes ratchet 6 and finger grip 4 down as far as they will go, i.e., as far down as lugs 44 (FIG. 7), moving in groove 36 (FIG. 3), will permit. However, as already mentioned above, in a certain position of lugs 44 relative to slots 38 in housing 2, finger grip 4 can be slightly lifted by pushing it up against the restoring force of spring 28. This feature can be used by the surgeon, should he decide to relocate needle 8 at a different spot, as long as notch 9 has not yet been captured by catch 58. All he has to do is to push up finger grip 4, which will cause the teeth 50 of ratchet 6 to lose contact with pawl 14. The surgeon can then move needle 8 back by pulling at the free end of suture 10.

The assembly of another embodiment of the suturing device according to this aspect of the present invention is shown in FIGS. 20 and 21. There are shown a housing 70, two needles 72, two needle pushers 74, two needle pullers 76, two pawls 78, two exit guides 80, two entrance guides 82, two needle-retaining rings 84 and two cover plates 86.

Housing 70 (FIGS. 22–24) is substantially prismatic and comprises a bore 88, the lower part of which is cylindrical and the upper part of which, tapering and thimble-like, accommodates and firmly holds the surgeon's finger. As in the previously-described embodiment, housing 70 is cut along a plane parallel to, but distant from, the axis of bore 88, so that the bore is exposed but still surrounds the surgeon's finger over more than 180°. Housing 70 is completely symmetrical laterally of the axis of bore 88, so that whatever is described about one side thereof, pertains also to the other side.

There are shown a substantially cylindrical depression or recess 90 (or rather, a segment of a recess, due to the cut-off front portion of housing 70) which houses most of the components described further below, a central hole 92 and a groove 94 at the bottom of recess 90, which accommodates needle 72. Also shown are two slots 96, 98, which accommodate exit guide 78 and entrance guide 80, respectively. Needle 72, including notch 73, is identical to that described above with reference to the previous embodiment, including suture 75 attached to its end.

Figure 25:
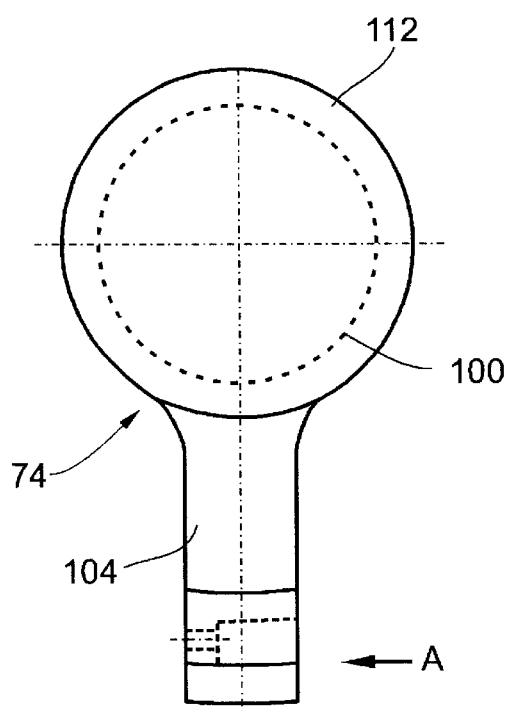
FIG. 25 is an elevational view of the needle pusher.
Figure 26:
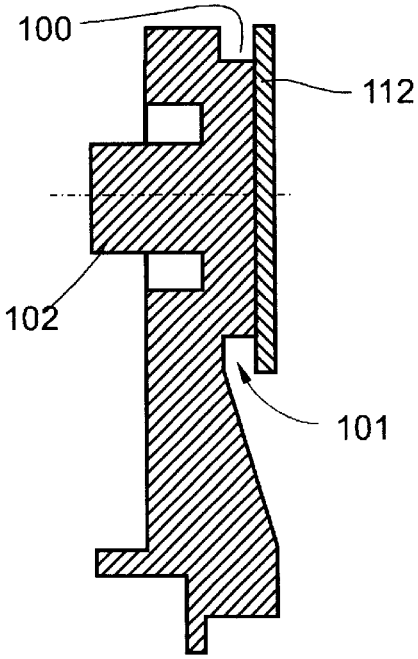
FIG. 26 is a cross-sectional view of the needle pusher of FIG. 25.

Needle pusher 74 is seen in FIG. 25 to consist of a central, substantially cylindrical portion 100, provided with a short shaft 102 (FIG. 26) fitting hole 92 in housing 70, and a radially extending arm 104. The rear of arm 104 is provided with a curved ledge 106 (FIG. 28), integral with which is a lug 108 having a hole 110 (FIG. 27), through which passes suture 75. By means of a disk 112, the cylindrical portion 100 is turned into a reel or drum 101 onto which cords 115 can be wound (see FIG. 20), for a purpose to be explained further below.

Figure 29:
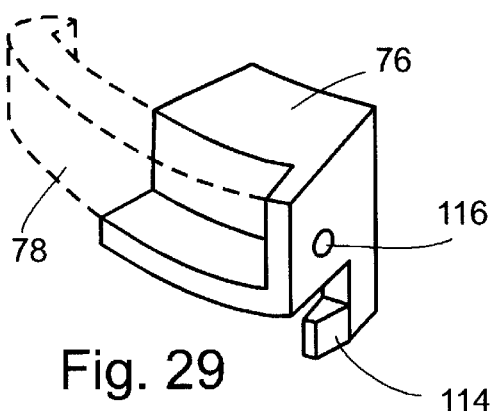
FIG. 29 is a perspective view of the needle puller, also indicating the position of the pusher-catching pawl.
Figure 30:
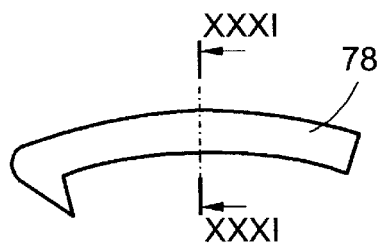
FIG. 30 is an elevational view of the pusher-catching pawl.
Figure 31:
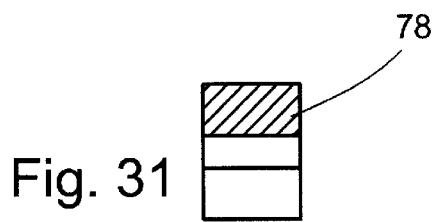
FIG. 31 is a cross-sectional view, along plane XXXI—XXXI, of the pawl of FIG. 30.
Figure 32:
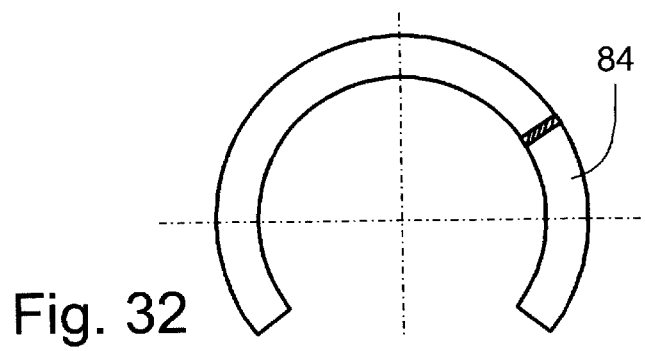
FIG. 32 illustrates a needle-retaining ring segment.

FIG. 29 represents needle puller 76, also indicating the position of pawl 78. Further shown is catch 114, the purpose of which is to engage notch 73 of needle 72 when the latter is to be returned into housing 70 after the stitch has been completed. Also shown is a hole 116, which passes through needle puller 76 and through which suture 75 is threaded. The initial position of needle puller 76 within housing 70 is clearly seen in FIGS. 20 and 21. While needle puller 76 and pawl 78 are shown here to be two different components, they can conceivably be produced as an integral whole, since, in any case, they must move together.

Exit and entrance guides 80 and 82 respectively are essentially the same as those used in the previous embodiment, plates with a flaring lead-in and a hole for the needle to pass through. Needle-retaining ring segment 84 (FIG. 32) fits into recess 90 (FIG. 22) and, together with groove 94, defines the duct in which needle 72 moves. Recesses 90, as well as slots 96, 98, are covered by cover plates 86, which also serve to retain needle pusher 74, needle puller 76 and pawl 78 (FIG. 20). A recess 118 in the lateral walls of housing 70 provides room into which pawl 78 is deflected when engaging needle pusher 74, as will be presently explained.

The above-described dual-needle embodiment of the suturing device according to this aspect of the present invention (FIGS. 20–31) is operated by the surgeon pulling a cord, using his other, free hand. To this end, two cords or threads are wound onto each drum 101 in two opposite senses of winding: for example, one blue cord for each drum 101 which, when pulled, will move its respective needle pusher 74 towards its exit guide 80, i.e., advancing its needle 72, and the other, a red cord for each drum, which, when pulled, will move is needle pusher 74 towards its entrance guide 82.

Figure 27:
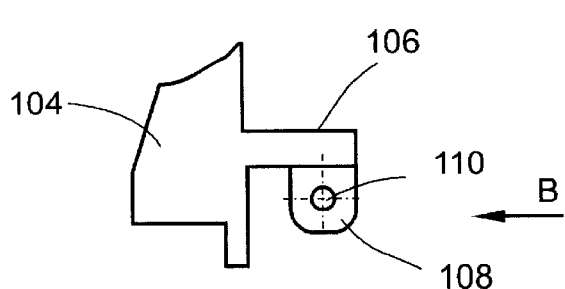
FIG. 27 is a partial view of the needle pusher in the direction of arrow A.
Figure 28:
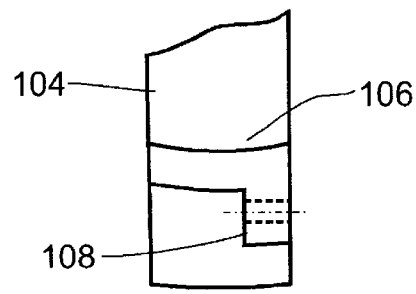
FIG. 28 is a view of the detail of FIG. 27 in the direction of arrow B.

After the proper location for the stitching operation has been found by palpation, the surgeon, by pulling both blue cords, thus advances needle pushers 74 towards exit guides 80, which serve also as stops to the advancing motion of needle pushers 74. By the time the surgeon feels that needle pushers 74 have been stopped, needle 72 have already commenced to re-enter housing 70 via entrance guides 82, with their notches 73 being captured by catches 114 (FIG. 29). Pulling the red cords will return needle pushers 74 in a direction towards entrance guide 82 and permit pawl return needle pushers 74 in a direction towards entrance guide 82 and permit pawl 78 to capture needle pushers 74 by engaging lugs 108 (FIG. 27). Again pulling the blue cords will move needle pushers 74 again towards exit guide 80, dragging along pawl 78 and needle pullers 76 (attached to, or integral with, pawls 78), thus, by means of their catches 114, returning needles 72 into housing 70. The needle driver may then be withdrawn.

Figure 33:
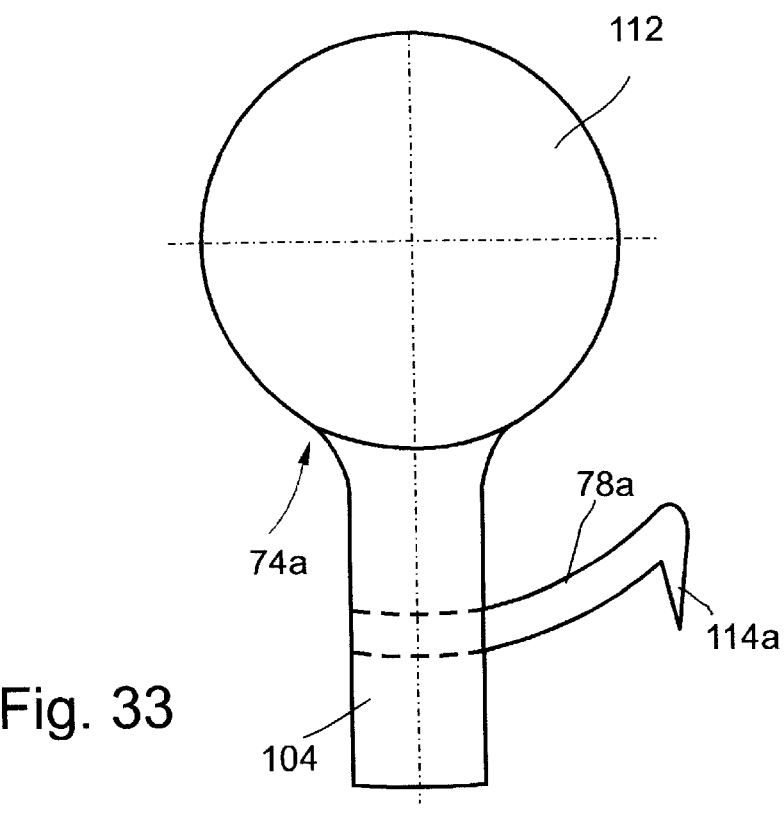
FIG. 33 is an elevational view of a variant of the needle pusher of FIG. 25.

A variant of needle pusher 74 is seen in FIG. 33. In the final stage of the proceedings, after the tip of needle 72, including notch 73, has already re-entered housing 70, the variant needle pusher 74A also serves as needle puller, obviating the need for a separate needle puller 76 (FIG. 29). In the original embodiment, pawl 78, being part of needle puller 76, merely serves as a mechanical link to hitch needle puller 76 to needle pusher 74, to enable the latter to complete withdrawal of needle 72. In the above variant, needle pusher 74A functions also as needle puller 76 as soon as, the red cord having been pulled, paul 78A, now part of needle pusher 74A, engages needle notch 73 with its catch 114A. Pulling now the blue cord will cause needle pusher 74A to move towards exit guide 80, dragging along needle 72 until it is fully inside housing 70.

Use of this variant also requires a slight modification in housing 70. Recess 118 in the walls of housing 70, which provided room for pawl 78 to be deflected into, must now be transferred to the other side of the needle path.

Using a dual-needle driver makes it possible to simultaneously place one stitch on either side of the urethra, or to place, in two successive steps, two stitches on either side thereof, in which case the needle driver has to be replaced prior to the second step.

Figure 33A:
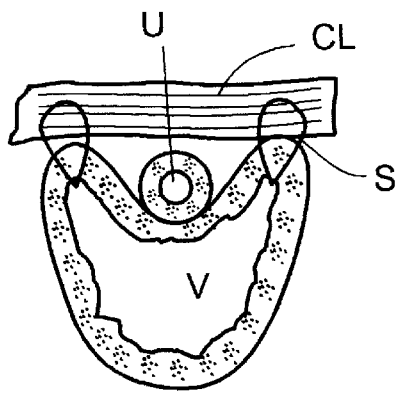
FIG. 33A is a schematic representation of the vagina and the urethra after a surgical procedure is completed using any of the devices described in FIGS. 1–33.
Figure 41:
Figure 42:
Figure 43:
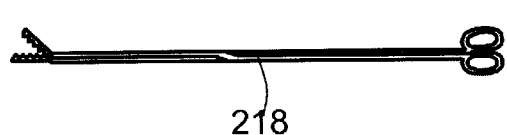

FIG. 33A is a schematic representation of the vagina and the urethra after the surgical procedure is completed, with V indicating the vagina; U, the urethra; CL, Cooper's ligament; and S, suture stitches.

Obviously, both the first and second embodiments of the suturing device according to this aspect of the invention will have to be produced in a range of different sizes to allow for the different sizes of the surgeons' fingers, or as further detailed hereinunder, adapters can be employed.

Although in the second, above-described embodiment of the suturing device, the needles are maneuvered by alternatingly pulling cords, embodiments are also envisaged in which the needles are manipulated by manual, electric or hydraulic actuators controlled by the surgeon, examples of which, in context of the following aspects of the invention are provided hereinbelow.

The first embodiment of this aspect of the present invention was experimentally found limiting in applications requiring high precision, because in order to advance the needle, the surgeon has to rotate his or her finger, thus operating the ratchet. The second embodiment of this aspect of the present invention was found to be somewhat limiting because pulling the cords (i) fails to give a surgeon a feeling of degree; and (ii) in some cases results in displacement of the device.

In search for improvements, the inventors realized several configurations which are further described hereinunder with reference to FIGS. 34–76, which, on one hand, broaden the scope of the invention, while, on the other hand, in preferred embodiments, overcome one or more of the limitations associated with the so far described aspects of the invention.

Thus, as shown in FIGS. 34–35, according to another aspect of the present invention there is provided a finger-mounted device 200 or 202 for guiding a surgical instrument. Device 200 or 202 comprising a thimble-like element 204 which is adapted to surround at least a portion of a surgeon's finger, while at least partially exposing the ventral tactile portions of the distal phalanx thereof, which tactile portions extending from the finger tip just underneath the nail and down to joint, so as to enable the surgeon to tactile sense a body location to be operated. Thimble-like element 204 is formed with at least one longitudinal guiding tunnel or housing 206 formed within a wall thereof. Longitudinal guiding tunnel 206 serves for guiding a surgical instrument therethrough, so as to enable the surgeon to operate a body location. Thus, by mounting device 200 over the dorsal portion of the distal phalanx of a finger, the surgeon entire ventral tactile portions of the distal phalanx thereof, extending from the finger tip just underneath the nail and down to joint are exposed for tactile sensing, while, by mounting device 200 over the ventral portion of the distal phalanx of a finger, or alternatively, by mounting device 202 over the distal phalanx of a finger, only the surgeon finger's tip is exposed for tactile sensing. Thus, in both cases, the most nervated and therefore tactile sensitive portion of the ventral tactile portions of the distal phalanx of the surgeon's finger, i.e., the finger's tip, just underneath the nail, are exposed for tactile sensing.

Figure 44:
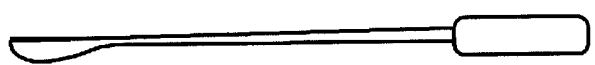
Figure 45:
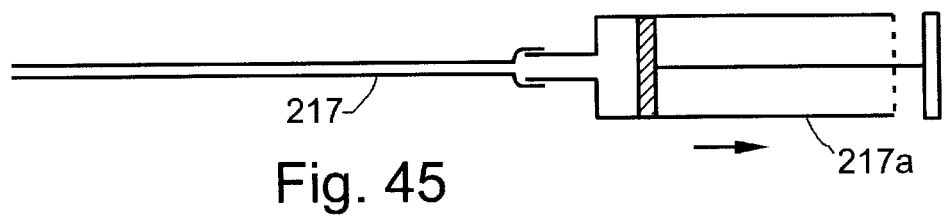
Figure 46:
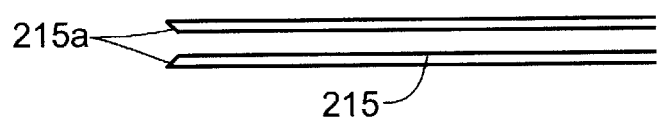

The surgical tool insertable through housing 206 of device 200 or 202 according to the present invention can be of any type. Examples include, but are not limited to, a surgical needle 210 (FIGS. 36, 37) or a needle 211 carrying a surgical anchor ejectable therefrom 211A (FIG. 38) both holding a suture or cord 210A, a puncturing device 212 (FIG. 39), an injection needle 213, which is shown connected at a proximal end thereof to a syringe 213A (FIG. 40), a capillary 214 (FIG. 41), a puncturing capillary 215, shown to have sharp distal edges 215A (FIG. 46), a miniaturized surgical grasper 216 (FIG. 42), a miniaturized aspiration capillary 217, shown connected to a syringe 217A (FIG. 45), miniaturized surgical scissors 218 (FIG. 43) and a miniaturized blade 219 (FIG. 44).

According to another aspect of the present invention there is provided a finger-guided surgical instrument which includes a thimble-like element 204 essentially as described above and which is, as described above, adapted to surround at least a portion of a surgeon's finger, while at least partially exposing the ventral tactile portions of the distal phalanx thereof, so as to enable the surgeon to tactile sense a body location to be operated. In contrast, with the construction of housing 206 of devices 200 or 202, the housing of the finger-guided surgical instrument according to this aspect of the present invention is occupied at al times, as further detailed and exemplified below, by a surgical tool or a portion thereof, and a mechanism for its operation. Thus, the finger-guided surgical instrument further includes an ejectable surgical tool which is engaged within a housing formed within, or connected to, a wall of the thimble-like element; and a mechanism for ejecting the surgical tool from the thimble-like element, so as to enable the surgeon to operate a body location. Specific examples of finger-guided surgical instruments according to various aspects of the present invention are further described hereinunder, followed by general features which are preferably common to all of the finger-guided surgical instruments of the present invention.

Thus, as shown in FIGS. 47–61, according to yet another aspect of the present invention there is provided a finger-guided surgical instrument which serves as a finger-guided suturing device. The device includes a thimble-like element 300, which is adapted to surround a portion of a surgeon's finger, while exposing the ventral tactile portions of the distal phalanx thereof, so as to enable the surgeon to tactile sense a body location to be operated.

According to a preferred embodiment of this aspect of the present invention thimble-like element 300 is constructed so as to be mounted over a dorsal side of the distal phalanx of the surgeon's finger, thereby exposing the entire ventral tactile portions of the distal phalanx including the tip.

Figure 47:
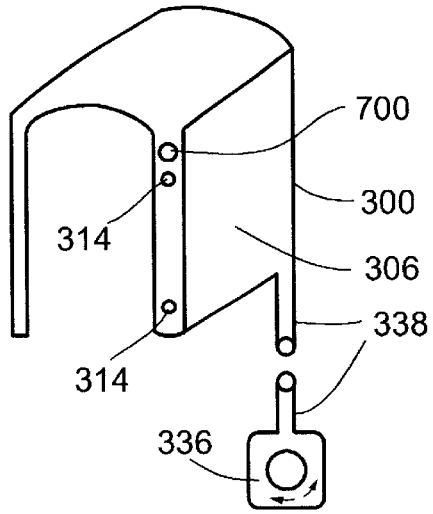
FIG. 47 is a perspective view of a finger-guided suturing device according to another aspect of the present invention, in which an ejected needle follows a circular path which is on a plane which parallels a plane traversing a surgeon's finger from top to bottom.
Figure 48:
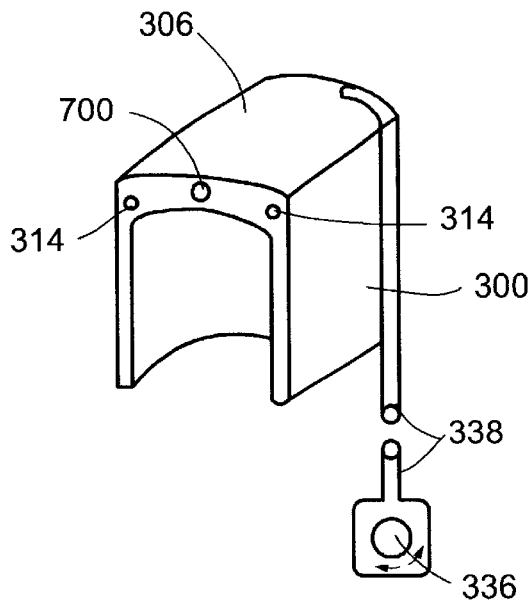
FIG. 48 is a perspective view of a finger-guided suturing device according to another aspect of the present invention, in which an ejected needle follows a circular path which is on a plane which is perpendicular to the surgeon's finger.
Figure 49:
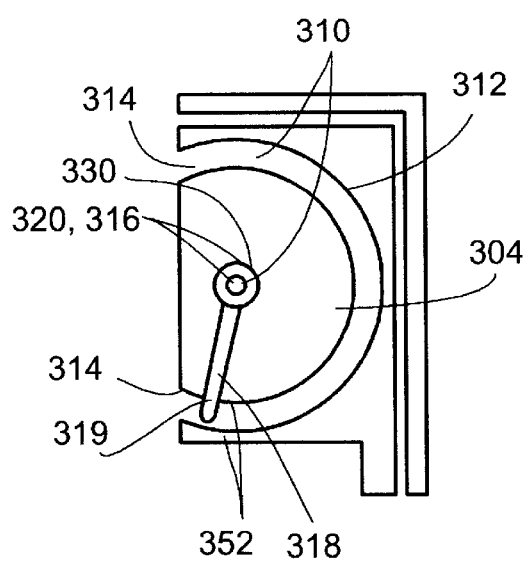
FIG. 49 is a cross sectional view of a housing engaged in a side wall of the device of FIG. 47 or a front wall of the device of FIG. 48.
Figure 50A:
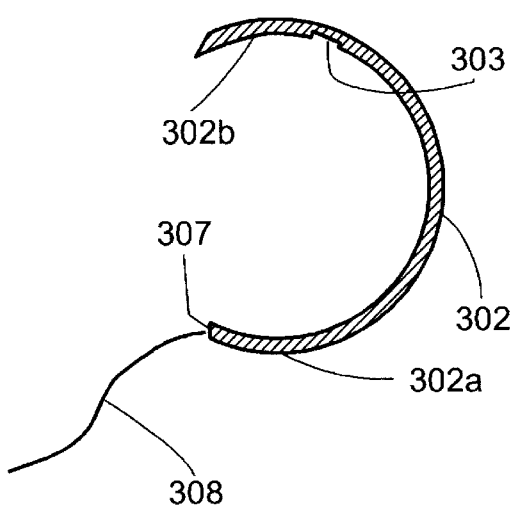
FIGS. 50A and 50B show semi-circular needles employed in the devices in FIGS. 47–48.
Figure 50B:
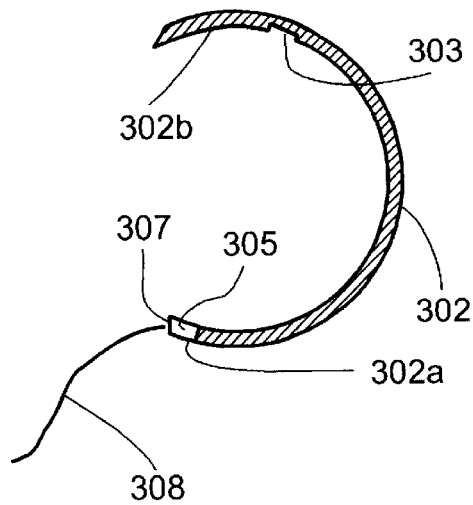

The device according to this aspect of the present invention further includes an ejectable, substantially semi-circular, surgical needle 302 which is engaged within a housing 304, which is formed within, or connected to, a wall 306 of thimble-like element. As shown in FIG. 47, wall 306 can be a side wall of member 300, or alternatively, as shown in FIG. 48, wall 306 can be a front wall of member 300. Needle 302 serves for holding and guiding a suture 308 which is attached at one end thereof to substantially semi-circular surgical needle 302. The suturing device according to this aspect of the present invention further includes a mechanism 310 for ejecting surgical needle in a circular path through an ejection opening in housing from thimble-like element and thereafter withdrawing surgical needle back into thimble-like element through a withdrawal opening in housing, so as to enable the surgeon to suture body location.

Mechanism 310 of the suturing device according to this aspect of the present invention includes a substantially semi-circular channel 312 formed in housing 304 and connecting ejection and withdrawal openings 314 and which fully engages substantially semi-circular surgical needle 302 before its ejection and following its withdrawal, so as to direct substantially semi-circular surgical needle in circular path around a virtual axis 316. Mechanism 310 further includes a remotely operated rotating arm 318 rotatably engaged in hosing 304 and rotatable about a hinge 320. Rotating arm 318 is designed to eject substantially semi-circular surgical needle 302 through ejection opening 314 by pushing a rear portion 302A of substantially semi-circular surgical needle 302 and rotating arm 318 is further designed to withdraw substantially semi-circular surgical needle 302 through withdrawal opening 314 by pulling a front portion 302B of substantially semi-circular surgical needle 302.

According to one embodiment of the present invention, and as specifically shown in FIGS. 49, and 50–54A, virtual axis 316 and hinge 320 are co-positioned. However, according to another preferred embodiment of the present invention, and as specifically shown in FIGS. 56, and 59, virtual axis 316 and hinge 320 are offset, whereas rotating arm 318 is an extendible-retractable arm, which is shown isolated in FIG. 55 to include a first, substantially hollow, segment 322 integrally formed with, or connected to, hinge 320 and including an extending spring element 324, and a second segment 326 extendibly-retractably accepted within the hollow of first segment 322, so as to be extended by the action of element 324 and retracted against the action of element 324. Segment 322 is preferably formed to include a stoppage so as to prevent the complete separation of segments 322 and 326. This latter configuration allows farther ejection of needle 302 in applications wherein such farther ejection is required. It will be appreciated that a configuration in which lesser ejection of needle 302 in applications wherein such lesser ejection is required is realizable, for example, by swooping the locations of hinge 320 and virtual axis 316. Alternatively, both hinge 320 and virtual axis 316 can be relocated farther away from openings 314 to otherwise achieve a similar result.

According to a preferred embodiment of the present invention substantially semi-circular surgical needle 302 is formed with a notch 303 (FIGS. 50A–B) at front portion 302B. Notch 303 is designed to accept a distal end 319 of rotating arm 318. A second notch 305 (FIG. 50B) can be formed at rear portion 302A of needle 302 which is also designed to accept distal end 319 of rotating arm 318. Alternatively, or additionally, substantially semi-circular surgical needle 302 is formed with a blunt rear end 307 (FIGS. 50A–B) which is designed to be pushed by rotating arm 318.

Remotely operated rotating arm 318 includes a rotating wheel 330 portion rotatable about hinge 320 and an arm portion 332 connected to, or integrally formed with, rotating wheel portion 330. Mechanism 310 further includes a remote rotation relay 334 which serves for relaying rotary motion from a remote rotatable actuator 336 to rotating wheel portion 330 for effecting rotation of rotating arm 318. According to a preferred embodiment, a flexible tube 338 connects between housing 304 and remote rotatable actuator 336, tube engaging remote rotation relay.

Figure 51:
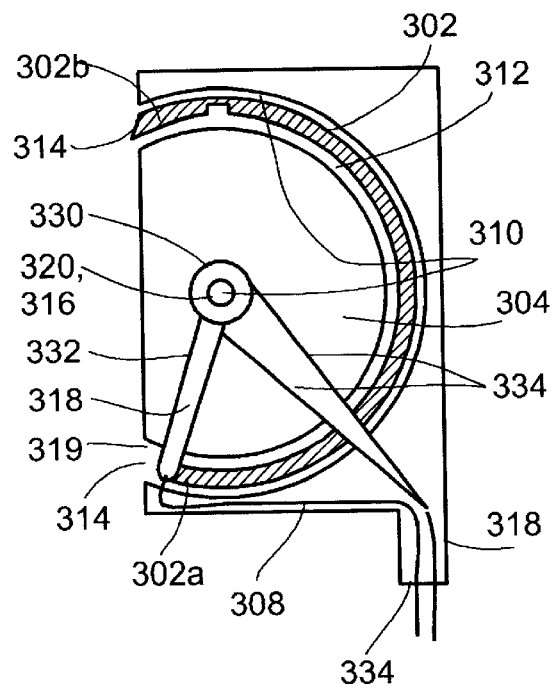
FIGS. 51–54A are cross sectional views of steps in the ejection and withdrawal of a semi-circular needle from and into the device of FIG. 47 or FIG. 48 according to one embodiment of the present invention, according to which a hinge of a rotating arm pushing or pulling the needle is colocalized with a virtual axis around which the needle is translocated.
Figure 52:
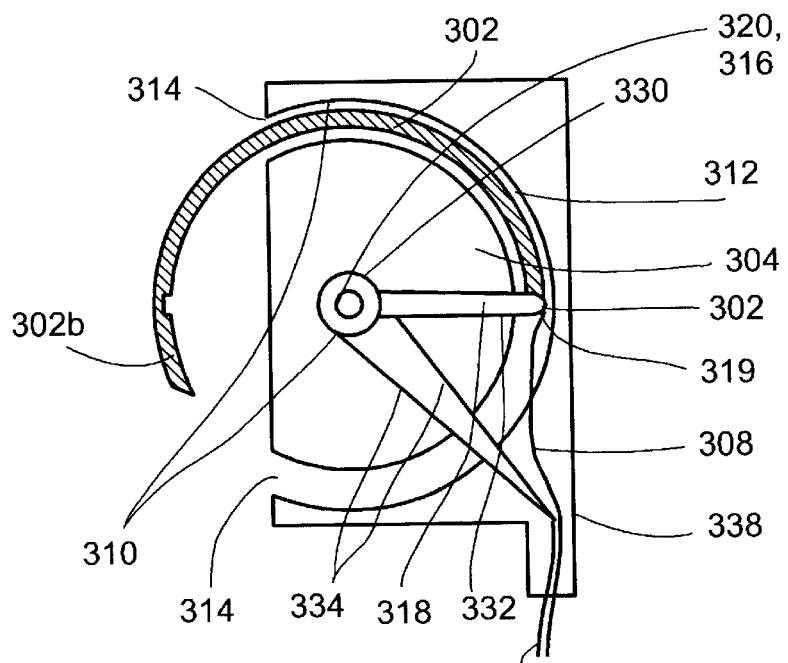
Figure 53:
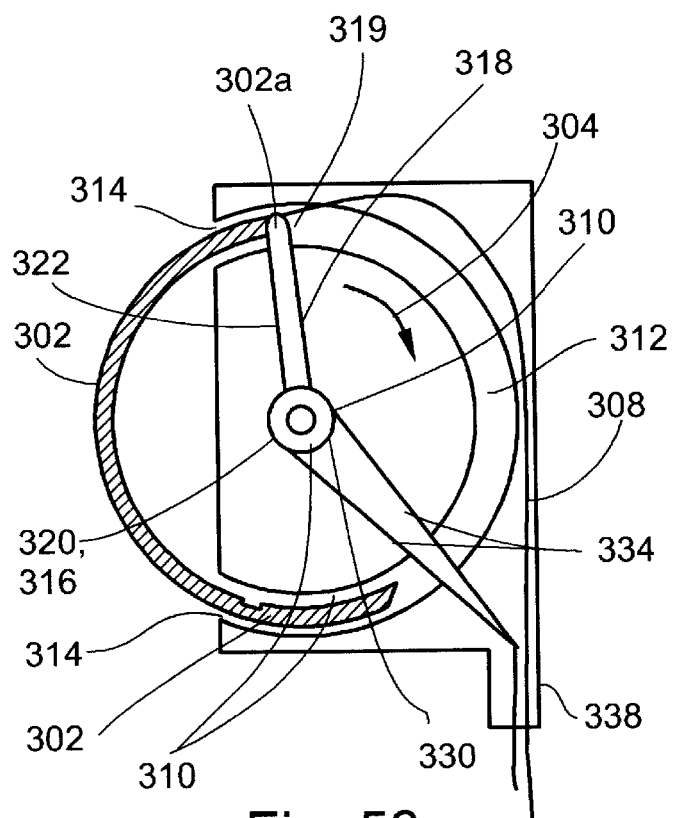
Figure 54:
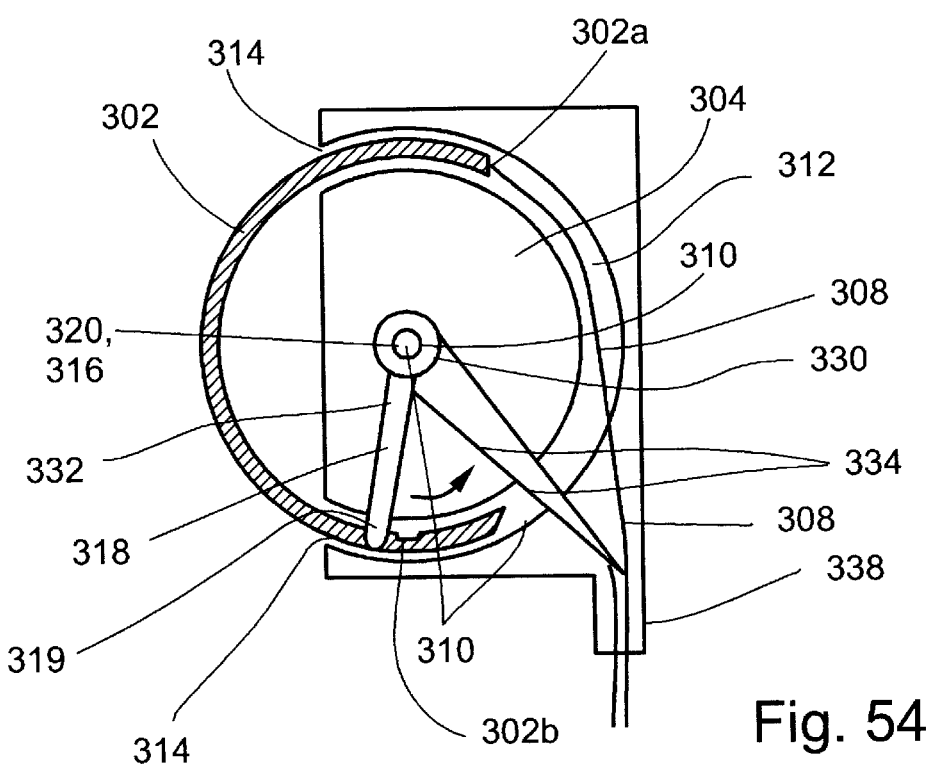
Figure 54A:
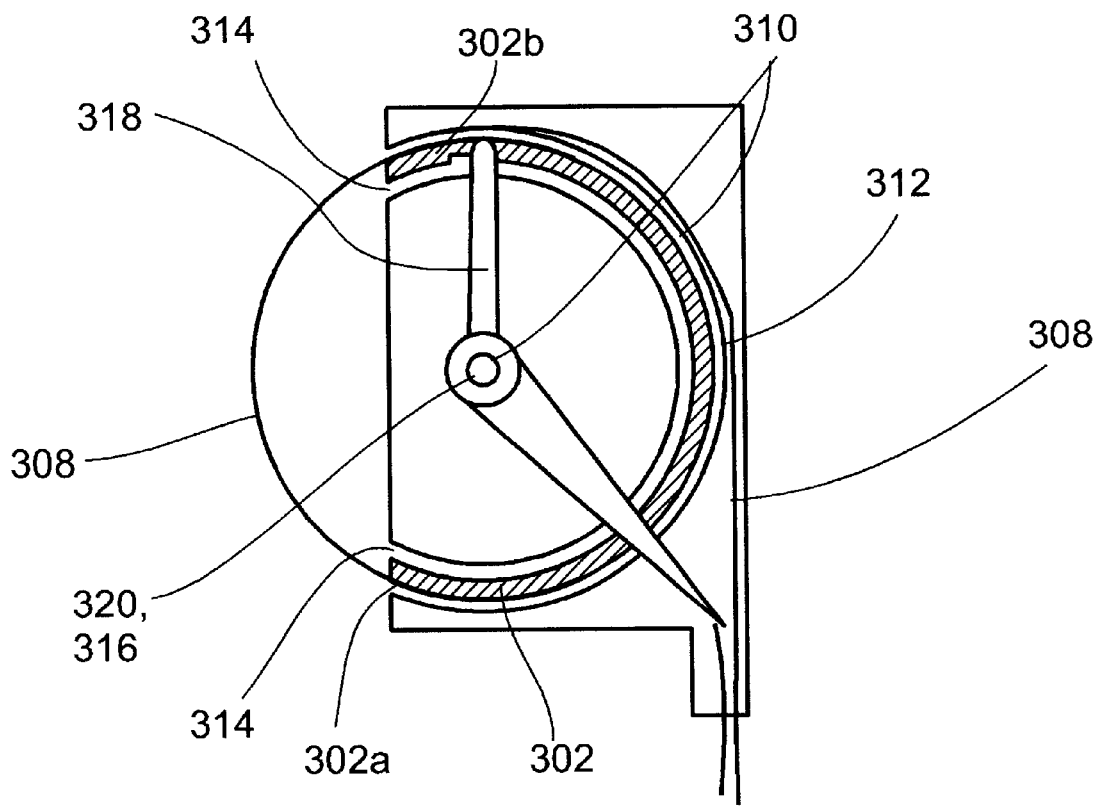
Figure 55:
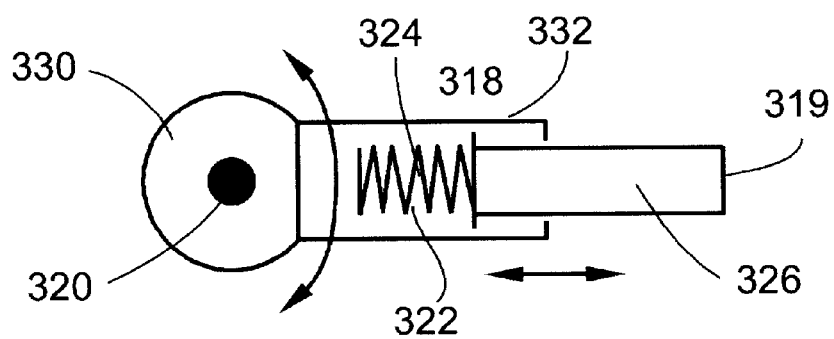
FIG. 55 is a cross sectional view of extendible-retractable rotating arm used for pushing or pulling the needle according to another embodiment of the present invention.
Figures 56, 57:
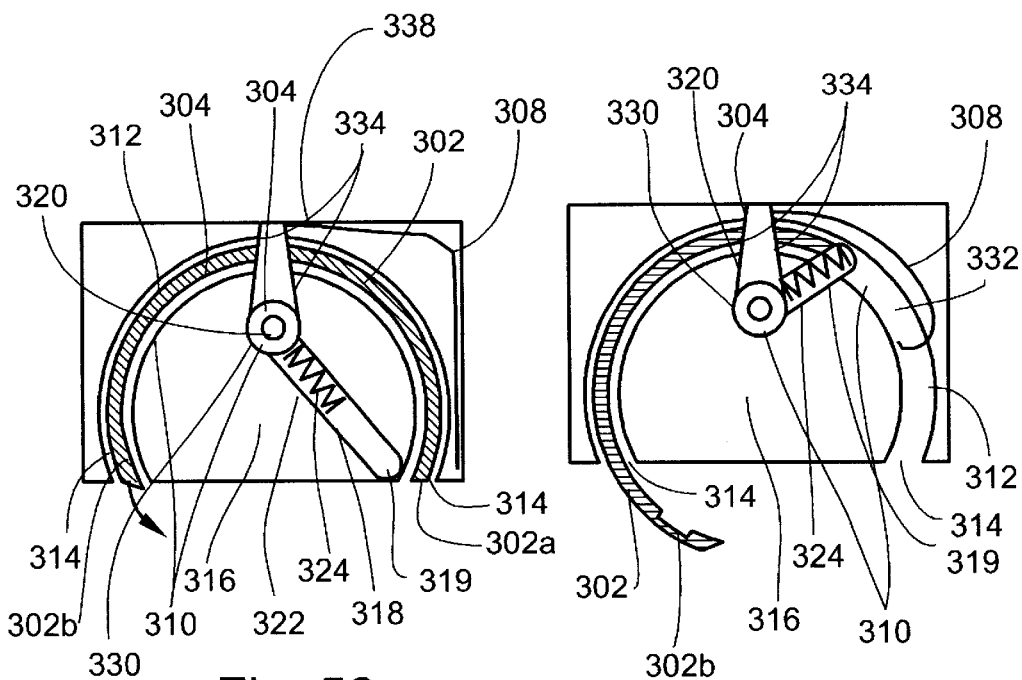
FIGS. 56–59 are cross sectional views of steps in the ejection and withdrawal of a semi-circular needle from and into the device of FIG. 47 or FIG. 48 according to another embodiment of the present invention, according to which the hinge of the extendible-retractable rotating arm pushing or pulling the needle is localized in offset with respect to the virtual axis around which the needle is translocated, to thereby achieve farther ejection of the needle.
Figures 58, 59:
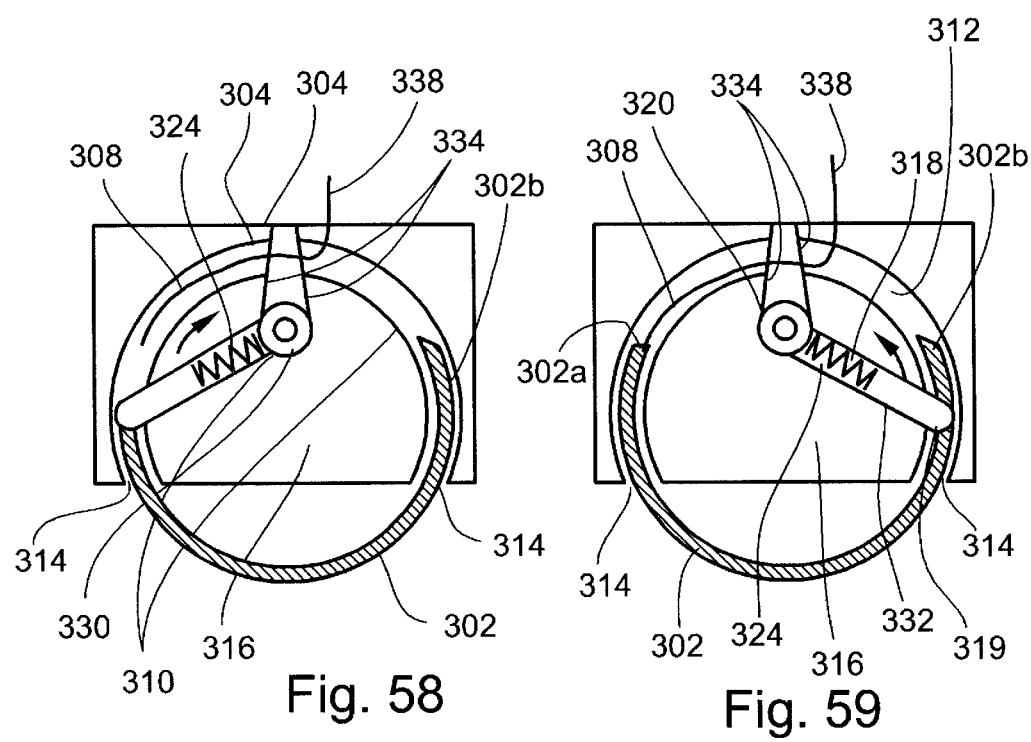
Figure 62:
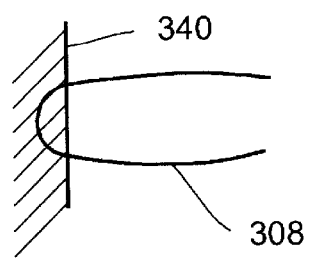
FIG. 62 shows a suture inserted in a tissue using the devices of FIGS. 47 or 48.

Thus, as shown in sequence in FIGS. 51–54A and in FIGS. 56–59, in a starting position (FIGS. 51 and 56) needle 302 is fully engaged within housing 304, such that no parts thereof protrude from thimble-like element 300. For operation, as shown in FIGS. 51 and 56, arm 318 is positioned so as to push rear portion 302A of needle 302 upon rotation. As shown in FIGS. 52–53 and 57–58, arm 318 is rotated by operating actuator 336 so as to eject front portion 302B of needle 302 out of housing 304 through ejection opening 314 until rear front 302B approaches withdrawal opening 314, whereas rear portion 302A is just about to leave ejection opening 314. Then, as shown in FIGS. 54 and 59, arm 318 is counter rotated about 180° and distal end 319 thereof engages notch 303 of needle 308, which has just entered withdrawal opening 314. Then, as shown in FIG. 54A, arm 318 is rotated as before so as to complete a full cycle of needle 318. Since needle 318 is holding suture 308, as a result of the motion of needle 302, suture 308 follows the same circular path. Thus, as shown in FIG. 62, by appropriately locating the suturing device described herein against a tissue 340, one can, using the suturing device as describe, to suture the tissue as shown.

As already mentioned above, and as shown in FIG. 47, wall 306 can be a side wall of member 300, in which case the circular path taken by needle 302 is on a plane which substantially parallels a plane traversing the surgeon's finger from top to bottom or alternatively, as shown in FIG. 48, wall 306 can be a front wall of member 300, in which case the circular path taken by needle 302 is on a plane which is substantially perpendicular to the longitudinal axis of the surgeon's finger. In yet another configuration, the circular path taken by needle 302 is on a plane which substantially parallels a plane traversing the surgeon's finger from side to side.

Figure 60:
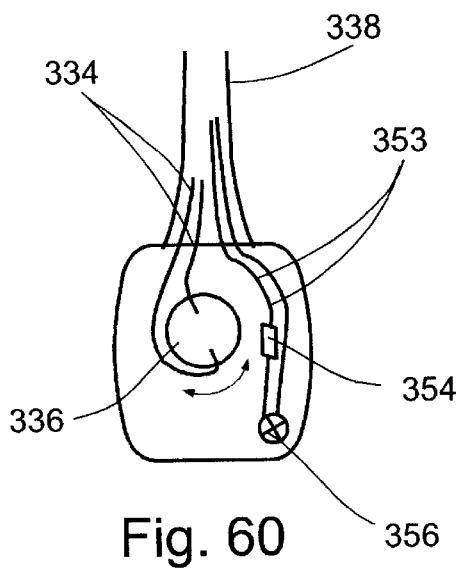
FIG. 60 is a cross sectional view of a mechanical/electrical remote control device used to operate and/or monitor the operation of the devices of FIGS. 47 and 48, showing a rotating actuator and one end of a rotation relay engaged thereby and which is used for rotating the rotating arm which pulls or pushes the needle, in addition, a portion of a reporting mechanism which is used for monitoring the needle ejection process is shown.
Figure 61:
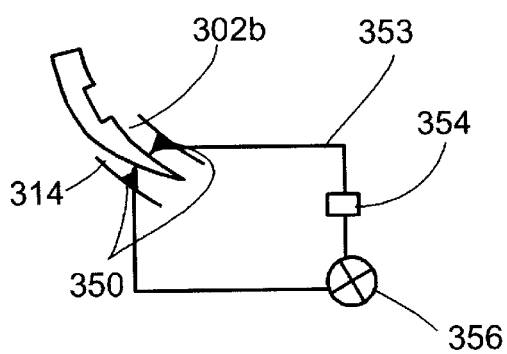
FIG. 61 shows another portion of the monitoring mechanism.

As specifically shown in FIG. 61, according to a preferred embodiment of this aspect of the present invention the suturing device further includes a reporting mechanism 350 for reporting situations, such as, but not limited to, a full ejection of substantially semi-circular surgical needle 302, a full withdrawal of substantially semi-circular surgical needle 302, a degree of ejection of substantially semi-circular surgical needle 302 and a degree of withdrawal of substantially semi-circular surgical needle 302. Reporting mechanism 350 according to a preferred embodiment includes two or more terminals 352 (FIGS. 49 and 61) located along the ejection/withdrawal path and which form a part of a circuit 353 which includes a power source 354 and a light and/or sound indicator 356 (FIG. 61), both are preferably located within a housing which also houses actuator 336 (FIG. 60). In the example shown in FIG. 61, when front portion of needle 302 enters withdrawal opening 314 between contacts 352, circuit 353 closes and indicator 356 operates, thereby indicating full ejection of substantially semi-circular surgical needle 302. It will be appreciated that by locating terminal at other locations along the path taken by needle 302 enables to similarly monitor a full withdrawal of substantially semi-circular surgical needle 302, a degree of ejection of substantially semi-circular surgical needle 302 and a degree of withdrawal of substantially semi-circular surgical needle 302.

It will be appreciated that, in contrast with the suturing device of the first aspect of the invention, no finger movement is required to eject and/or withdraw needle 302. It will further be appreciated that using actuator 336 and mechanism 350, one gains a high level of control and preciseness on the operation of the suturing device according to this aspect of the present invention.

Figure 63:
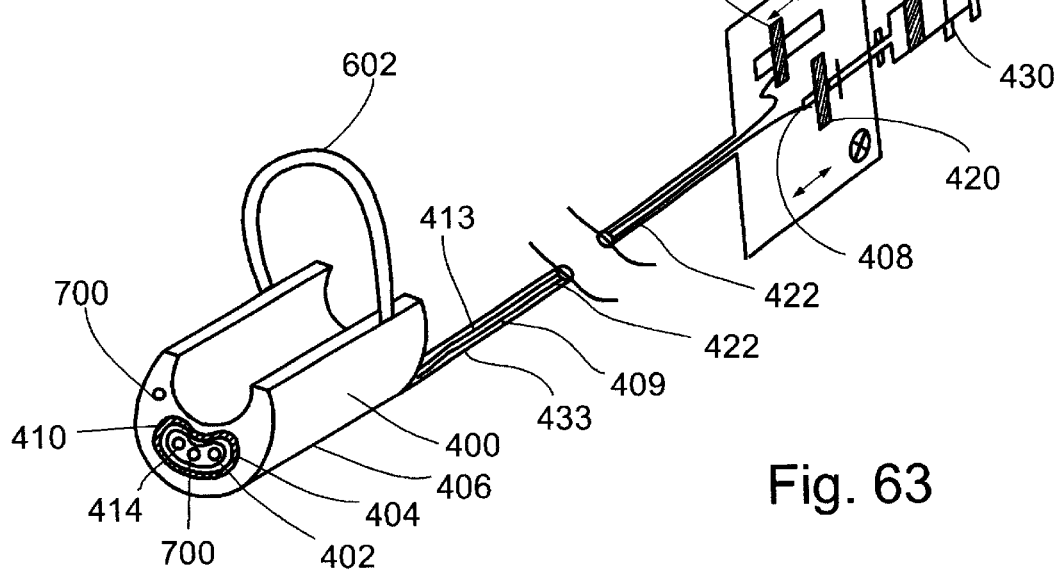
FIG. 63 is a perspective view of a finger-guided sampling device according to another aspect of the present invention, showing a capillary and a puncturing device thereof in their withdrawn position.
Figure 64:
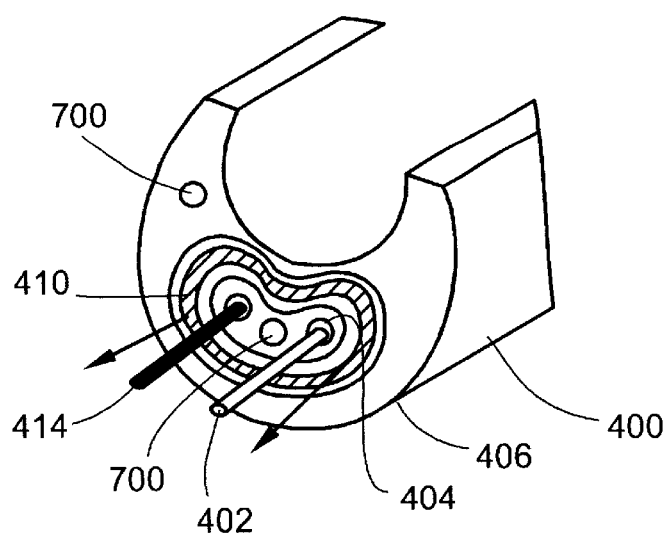
FIG. 64 is an enlarged perspective view of a portion of the finger-guided sampling device of FIG. 63, showing the capillary and the puncturing device thereof in their ejected position.
Figure 65:
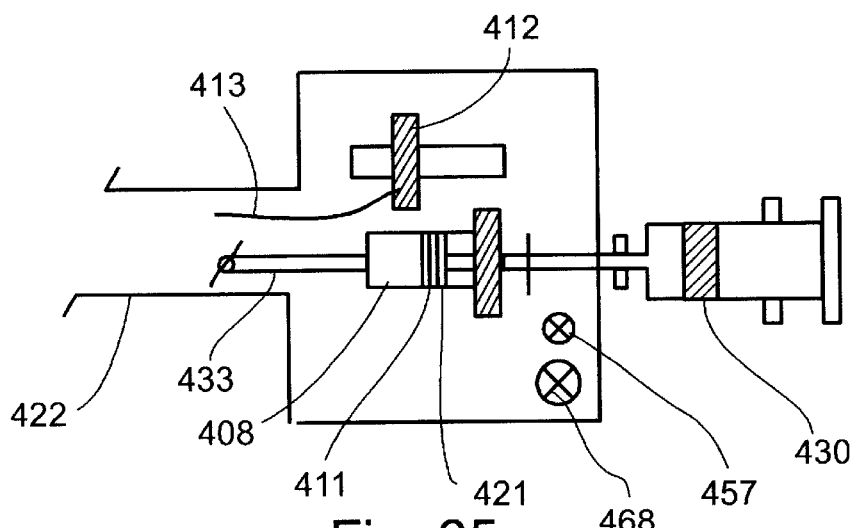
FIG. 65 is a top enlarged view of remote actuators employed for ejecting/withdrawing the capillary and the puncturing device.

As shown in FIGS. 63–65 according to yet another aspect of the present invention there is provided a finger-guided surgical instrument which serves as a sampling device for sampling a sample from a body location.

The sampling device includes a thimble-like element 400 which is adapted to surround at least a portion of a surgeon's finger, while at least partially exposing the ventral tactile portions of the distal phalanx thereof, so as to enable the surgeon to tactile sense a body location to be sampled.

According to a preferred embodiment thimble-like element 400 is constructed so as to be mounted over a ventral side of the distal phalanx of the surgeon's finger, thereby exposing the tip of the ventral tactile portion of the distal phalanx, underneath the nail.

The device further includes an ejectable capillary 402 which is engaged within a housing 404 formed in a wall, e.g., back wall 406, of thimble-like element 400. The device further includes a first mechanism 408 for ejecting ejectable capillary 402 from thimble-like element 400, so as to enable the surgeon to capillary sample the body location. Ejectable capillary 402 is preferably a translatably ejectable capillary, whereas first mechanism 408 is a remotely operated translatable ejectable mechanism, having an ejection relay 409 operated via a translating actuator 420, and which propagates along a tube 422 to translate capillary 402. Capillary 402 is ejectable in a direction generally in extension of a longitudinal axis of thimble like element 400.

According to a preferred embodiment of this aspect of the present invention the sampling device further includes a translatably ejectable sleeve 410 which is engaged within housing 404 and surrounds ejectable capillary and a second mechanism 412 including a translation relay 413 for ejecting translatably ejectable sleeve 410 from thimble-like element 400, so as to shield the sampled body location from surrounding body fluids while sampling. Sleeve 410 is ejectable in a direction generally in extension of a longitudinal axis of thimble like element 400.

According to another preferred embodiment of the sampling device according to this aspect of the present invention, the sampling device further includes an ejectable puncturing device 414 which is engaged within housing 404, wherein first mechanism 408 further serves for ejecting ejectable puncturing device 414 from thimble-like element 400, so as to enable the surgeon to wound the body location to be sampled. Device 414 is ejectable in a direction generally in extension of a longitudinal axis of thimble like element 400.

Figure 66:
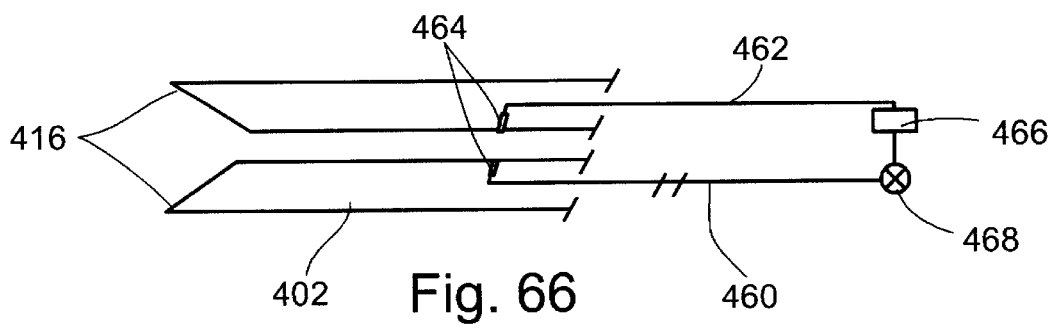
FIG. 66 is a cross sectional view of a capillary having sharp edges and which is equipped with a reporting mechanism for reporting the presence of electro conductive collected sample therein.
Figure 67:
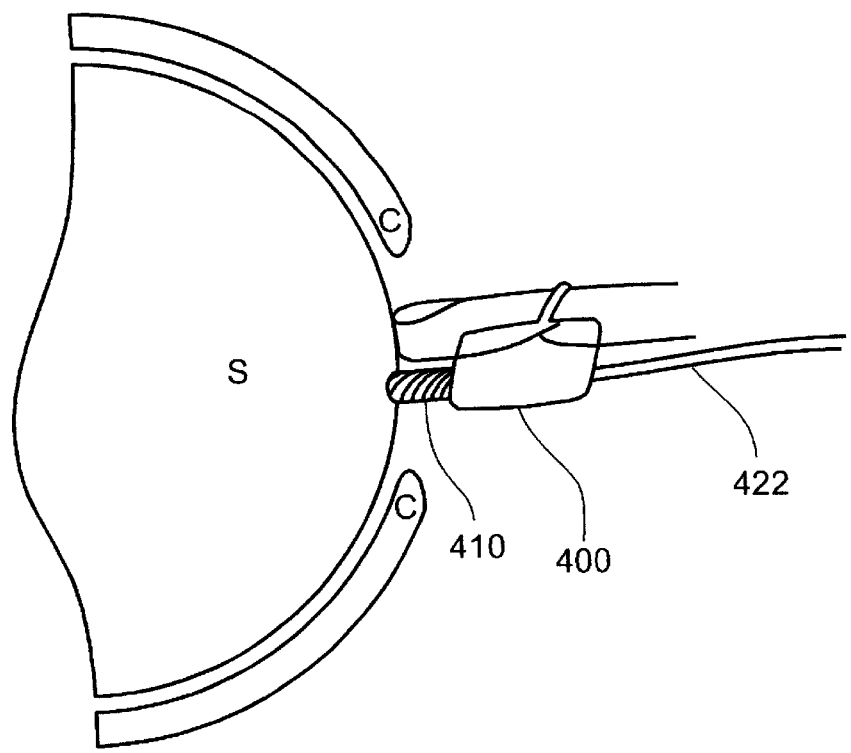
FIG. 67 shows the device of FIG. 63 mounted on a surgeon's pointing finger and used to sample a fetal scalp during labor, while the sleeve thereof is ejected, wherein C is the cervix and S is the fetal scalp.
Figure 68:
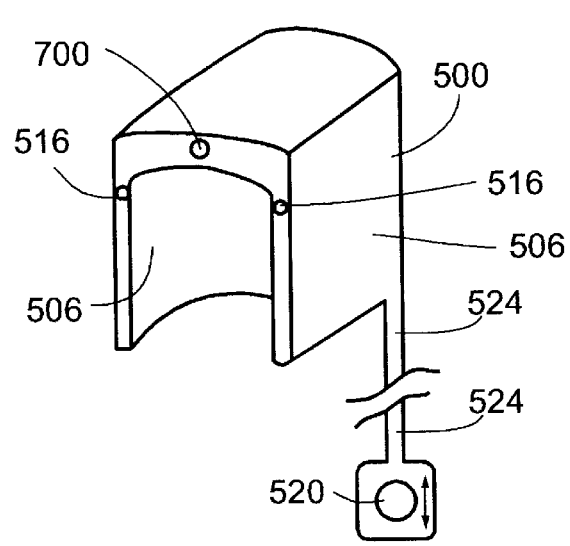
FIG. 68 is a perspective view of an anchor implanting device according to the present invention.
Figure 69:
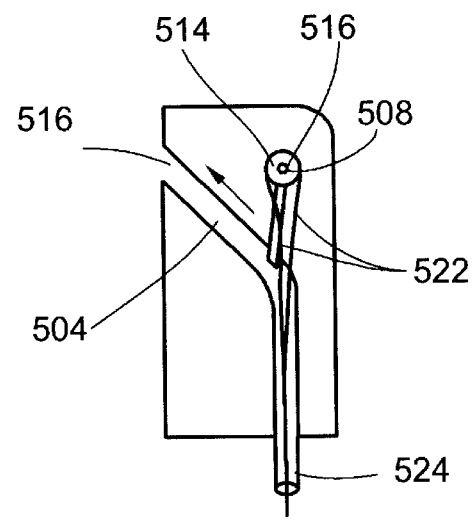
FIG. 69 is a cross sectional view of a single housing engaged in a wall of the device of FIG. 68.
Figure 73:
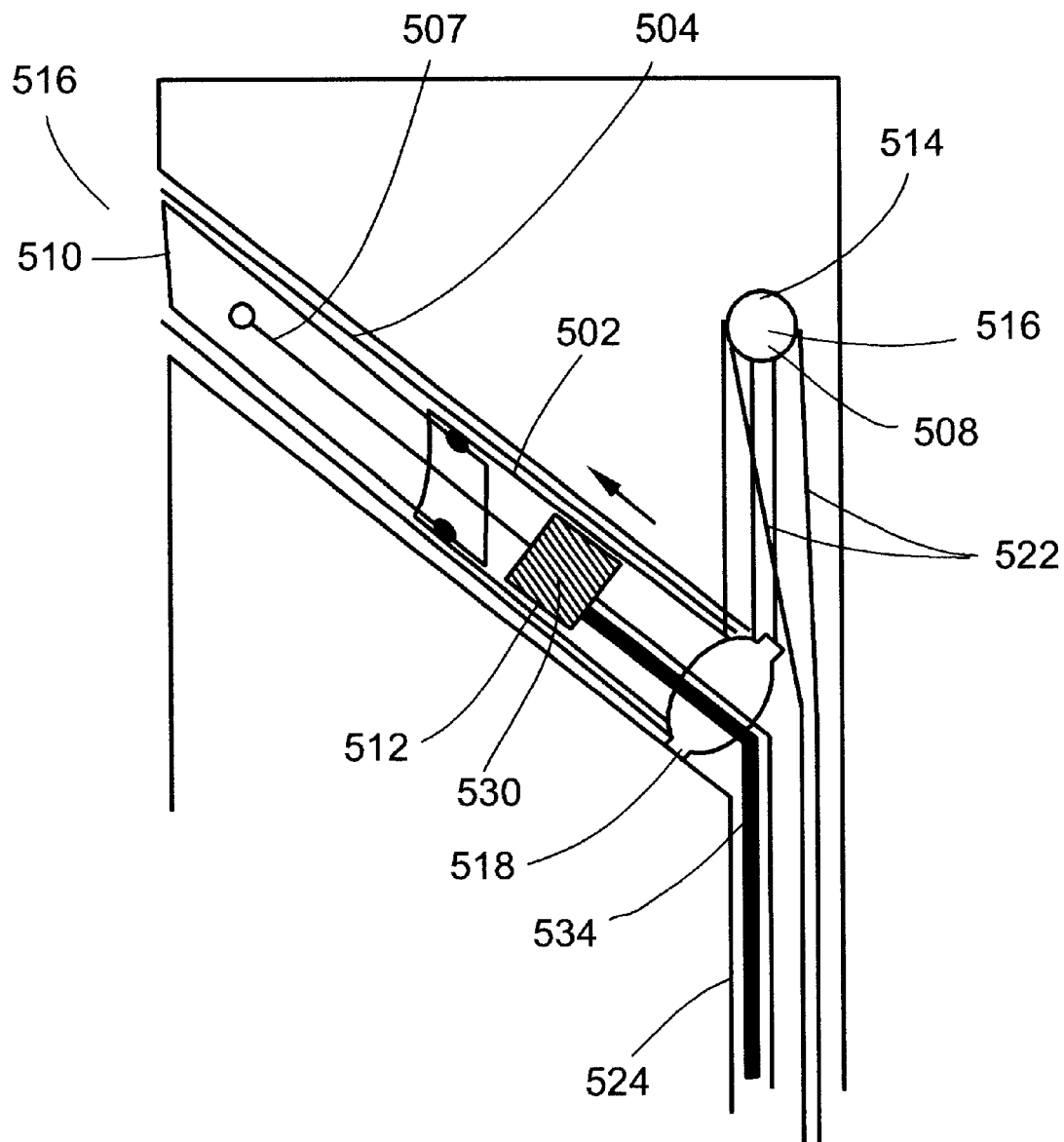
FIG. 73 is a cross section view of the anchor guiding element and the anchor guided thereby being in the housing of the device of FIG. 68.

According to an alternative embodiment of the sampling device according to this aspect of the present invention, and as specifically shown in FIG. 66, ejectable capillary 402 has sharp edges 416 so as to enable the surgeon to wound the body location, thereby obviating the need for puncturing device 414. In this case, ejectable capillary 402 is preferably a rotatably-translatably ejectable capillary, whereas first mechanism 408 is a remotely operated rotatable-translatable ejection mechanism (FIG. 65, shown as thread 411), having an ejection relay 409 operated via a rotating-translating actuator 421, and which rotatably propagates along tube 422 to rotatably translate capillary 402.

According to another preferred embodiment, ejectable capillary 302 is an ejectable aspiration capillary, whereas the sampling device further includes a remote aspirating device, such as a syringe 430, which is in fluid communication with ejectable aspiration capillary via a tube 433 which also serves as relay 409 is employed to aspirate a sample into capillary 402, thereby obviating the need to depend on capillary action for sample collection, enabling the collection of larger volumes in a single sampling session.

It will be appreciated that mechanisms 408 and 412 can be used to withdraw their respective tools, prior to the removal of the sampling device from the sampled body location, if so required, in order not to risk injuring the patient doing so.

According to a preferred embodiment of this aspect of the present invention the sampling device further includes a reporting mechanism 440 for reporting a situation, such as, but not limited to, a full ejection of capillary 402, sleeve 410 and/or device 414, a full withdrawal of capillary 402, sleeve 410 and/or device 414, a degree of ejection of capillary 402, sleeve 410 and/or device 414 and a degree of withdrawal of capillary 402, sleeve 410 and/or device 414. Reporting mechanism 440 operates in a fashion similar to mechanism 350 described hereinabove with respect to FIG. 61, whereby capillary 402, sleeve 410 and/or device 414 are conductive and the presence of portions thereof is determined by closing or opening an electrical circuit so as to activate or deactivate an indicator 457 (FIG. 65).

As specifically shown in FIG. 66, according to another preferred embodiment of this aspect of the present invention the sampling device further includes a reporting mechanism 460 in capillary 402 for reporting to the surgeon of a situation, such as, but not limited to, a presence of fluid in capillary 402 and a level of fluid in capillary 402. Since body fluids are conductive, such fluids serve to close circuit 462 by engaging a space between terminals 464, so as to enable a power source 466 to power an indicator 468.

As shown in FIGS. 68–74, according to still another aspect of the present invention there is provided yet another finger-guided surgical instrument which serves as an anchor implanting device. The anchor implanting device comprising a thimble-like element 500 which is adapted to surround at least a portion of a surgeon's finger while at least partially exposing the ventral tactile portions of the distal phalanx thereof, so as to enable the surgeon to tactile sense a body location into which anchor or a pair of anchors are to be implanted. Thimble-like element 500 is preferably constructed so as to be mounted over a dorsal side of the distal phalanx of the surgeon's finger, thereby exposing the entire ventral tactile portions of the distal phalanx.

The device further includes at least one ejectable anchor guiding element 502 which is engaged within at least one housing 504 which is formed within, or connected to, at least one wall, preferably side walls 506 of thimble-like element 500. The device further includes at least one first mechanism 508 for ejecting anchor guiding element(s) 504 from thimble-like element 500, so as to penetrate or come closer to a body location. The device further includes at least one ejectable anchor 510 engaged within ejectable anchor guiding element(s) 502, a cord 507 is connected thereto at a position so as to effect rotation and therefore efficient anchorage of anchor(s) 510 when anchored in the body location by pulling on cord 507. The device further includes at least one second mechanism 512 which serves for ejecting ejectable anchor(s) 510 from within ejectable anchor guiding element(s) 502, so as to enable the surgeon to anchor ejectable anchor(s) 510 in the body location.

According to a preferred embodiment of the present invention first mechanism(s) 508 include at least one remotely operated rotating arm 514 which is engaged in hosing 504 which is rotatable about a hinge 516. Arm(s) 514 are designed to eject ejectable anchor guiding element(s) 502 through at least one ejection opening 516 formed in housing(s) 504 by pushing rear portion(s) 518 of ejectable anchor guiding element(s) 502. According to a preferred embodiment, remotely operated rotating arm(s) 514 are further designed to withdraw ejectable anchor guiding element(s) 502 by pulling rear portion(s) 518 of ejectable anchor guiding element(s) in a reverse direction. According to a preferred embodiment arm(s) 514 are rotated by a shared remote rotation actuator 520 which rotates relay(s) 522 which pass through a tube 524 and surrounds rotating wheel(s) of arm(s) 514.

Second mechanism(s) 512 include at least one remotely operated translatable ejection mechanism 530 which serves for ejecting anchor(s) 510 from ejectable anchor guiding element(s) 502. Mechanism(s) 530 are operated via a translation actuator 532 and a translation relay 534 passing through tube 524.

Closed-open circuitries are preferably employed as a reporting mechanism for reporting a situation, such as but not limited to a full ejection of the at least one ejectable anchor, a full ejection of the at least one ejectable anchor guiding element, a full withdrawal of the at least one ejectable anchor guiding element, a degree of ejection of the at least one ejectable anchor guiding element and a degree of withdrawal of the at least one ejectable anchor guiding element. The operation of such circuitries are further described herein above with respect to other aspects of the present invention.

Figure 74:
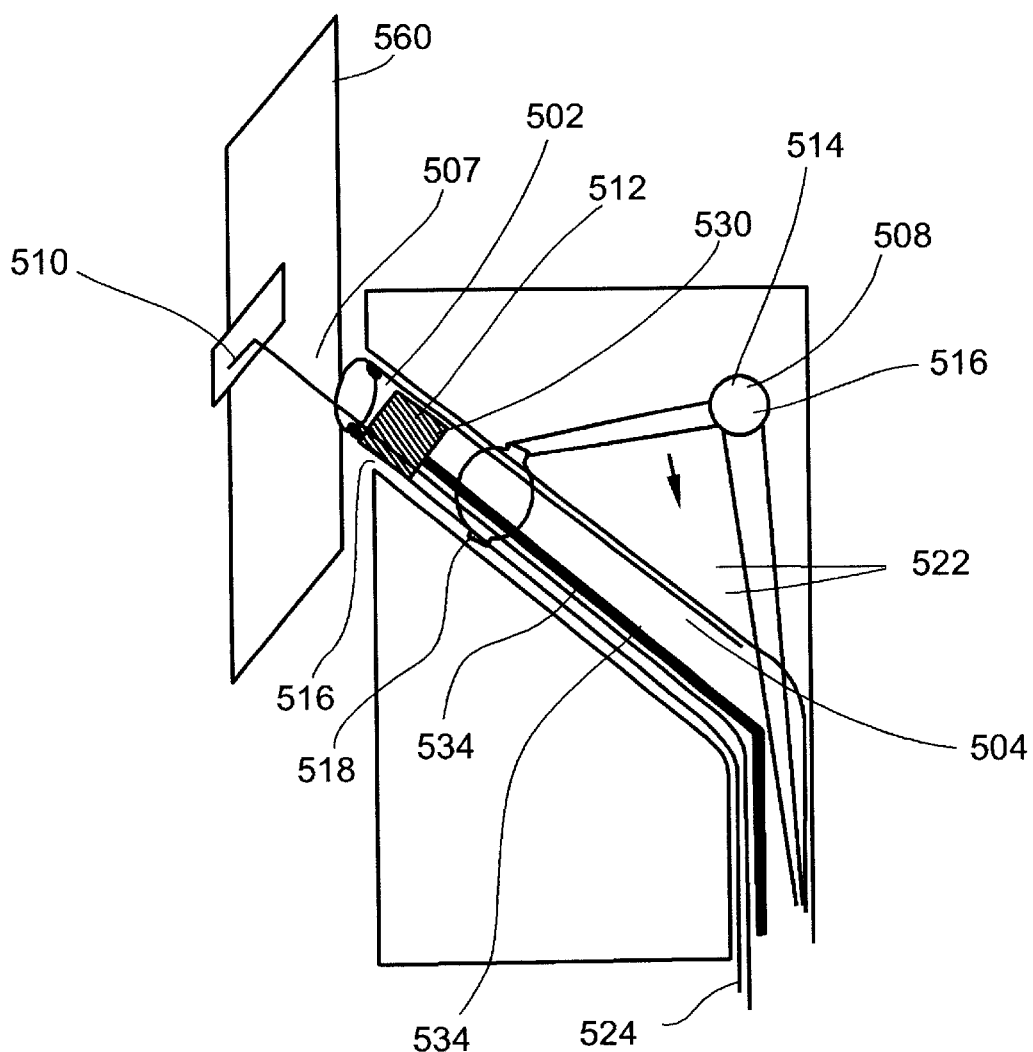
FIG. 74 is a cross section view of the anchor guiding element and the anchor guided thereby being ejected from the housing of the device of FIG. 68, while the anchor is ejected from the guiding element and anchored in a tissue.

Thus, as shown in FIG. 74, by first ejecting guiding elements 502 and then ejecting anchor(s) 510, the surgeon can anchor(s) 510 is a tissue 560. By pulling cord 507, the surgeon tilt's an anchor 507 so as to be strongly engaged within tissue 560.

The devices described hereinabove enjoy several advantages over prior art designs. All of the devices described include a thimble-like element which is designed to enable tactile sensing by a wearing finger. All of the devices include an ejectable surgical tool, which is withdrawn in a housing of the device and which is ejected only upon use. Thus, the devices according to the present invention allow the surgeon to sense a body location to be operated or treated while approaching the location without the disturbance of a permanently protruding surgical tool, tactile sense the location, and then, at the appropriate location, eject the tool to operate or treat the patient. In some embodiments, the ejection process is by a ratchet mechanism operated by rotating the surgeon's finger, whereas in other embodiments remote translation or rotation actuators are employed, which actuators are operable by the free hand of the surgeon.

The following sections describe some preferred embodiments, one or more of which can be applied to any of the devices of the preset invention. Some of these embodiments have already been described with respect to some of the described devices, but not others and are therefore repeated herein in a more generalized form.

Figure 75:
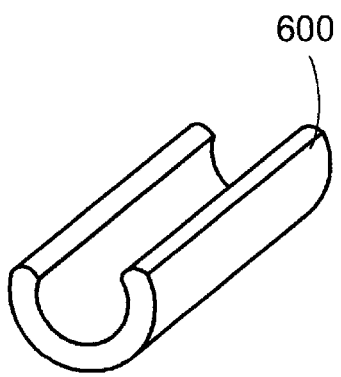
FIGS. 75–76 are perspective views of adapters according to the present invention.
Figure 76:
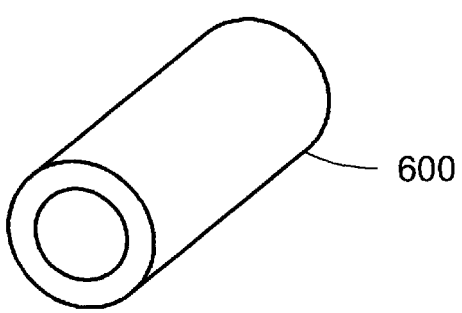

Thus, as shown in FIGS. 75 and 76, according to a preferred embodiment of the present invention, and in order to fit a plurality of fingers of a single surgeon, or in order to fit a single finger, such as the pointing finger, of a plurality of surgeons having fingers in a variety of thicknesses, the finger-mounted device for guiding a surgical instrument and/or the finger-guided surgical instrument according to the present invention further includes an adapter 600 which is insertable between the thimble-like element and the surgeon's finger, so as to adapt the finger-mounted device or the guided surgical instrument to fingers of different sizes.

As shown in FIG. 63, according to another preferred embodiments of the present invention any of the finger-mounted devices for guiding a surgical instrument and/or the finger-guided surgical instruments according to the present invention can include a supporting strap 602, for firmly mounting and supporting the device or instrument onto the surgeon's finger.

In preferred embodiments of the present invention the mechanism which is employed to eject a surgical tool out of the housing of the thimble-like element includes a first portion engaged within the housing and which is in contact with the ejectable surgical tool and a second, remote, portion extending out of the patient's body and which includes an actuator operable by a free hand of the surgeon, so as to eject the surgical tool from the thimble-like element. Alternatively, the mechanism includes a ratchet member disposed between the thimble-like element and the surgeon's finger, so as to eject the surgical tool from the thimble-like element by twisting back and forth the surgeon's finger. Any such mechanism is shown herein to also function for withdrawing the ejectable surgical tool back into the housing. Depending on the specific application, any one or more walls of the thimble like element can include a housing for engaging the ejectable surgical tool and at least a portion of the mechanism employed for its ejection. Thus, side, front and back walls can be used accordingly.

The thimble-like element employed in any of the aspects according to the present invention can be constructed so as to be mounted over a dorsal side of the distal phalanx of the surgeon's finger, thereby exposing the entire ventral tactile portions of the distal phalanx. Alternatively, the thimble-like element is constructed so as to fully surround the distal phalanx and expose the tip of the ventral tactile portion of the distal phalanx, just underneath the nail. Yet, alternatively, the thimble-like element is constructed so as to be mounted over a ventral side of the distal phalanx of the surgeon's finger and expose the tip of the ventral tactile portion of the distal phalanx. In some embodiments of the present invention the surgical tool is ejectable in a direction generally in extension of a longitudinal axis of the thimble like element. However, in other embodiments, the surgical tool is ejectable in a circular path which can be on a plane which substantially parallels a plane traversing the surgeon's finger from top to bottom, on a plane which substantially parallels a plane traversing the surgeon's finger from side to side, or on a plane which is substantially perpendicular to the longitudinal axis of the surgeon's finger.

Throughout the specification examples have been given to the use of any one of a plurality of ejectable surgical tools in context of the finger-mounted device or surgical instrument of the present invention. Thus, a surgical needle, a needle carrying a surgical anchor ejectable therefrom, a puncturing device, an injection needle, a capillary, a puncturing capillary, a miniaturized surgical grasper, miniaturized surgical scissors, a miniaturized blade and/or an aspiration capillary can all be either guided via the finger mounted device and/or ejectably and operatively engaged with the finger guided surgical tool according to the present invention.

According to preferred embodiments, the finger-mounted device for guiding a surgical instrument and/or the finger-guided surgical instrument include a reporting mechanism for reporting at least one situation selected from the group consisting of a full ejection of the surgical tool, a full withdrawal of the surgical tool, a degree of ejection of the surgical tool and a degree of withdrawal of the surgical tool.

As shown, for example, in FIGS. 34, 35, 47, 48, 63, 64 and 68, according to a preferred embodiment of the present invention the finger-mounted device and/or the finger-guided surgical instrument further includes at least one optical head 700 engaged by the thimble-like element thereof. Optical head 700 communicates with a monitor or any other display for presenting the surgeon with details of the path to the body location to be treated or the treated body location itself prior, during or after treatment. Optical head 700 can include a miniaturized camera and/or preferably a bundle of optic-fibers to generate an image which is representable on a monitor or any other display. In addition, optical head 700 can include one or more optical elements such as, but not limited to, lenses, prisms, reflectors and the like. Of particular interest is a fish-eye lens which can be used to provide a larger field of view for optical head 700.

According to a preferred embodiment of the present invention, optical head 700 includes a lens for focusing imagery data onto a boundle of fiber optics which transmit the imagery data to a sensor, such as, but not limited to, a camera which is remote and connectable to the device or instrument. This feature is of importance in cases the device or instrument are of a disposal type.

The following sections relate to the use of the finger-guided surgical instruments herein described in various surgical procedures. It is understood that these procedures are provided as examples and are not to be taken as limiting. It will be appreciated by one of skills in the art that many other procedures can be performed using the instruments of the present invention. More particularly, the following exemplary surgical procedures describe surgical protocols in which a single finger of a surgeon is inserted intrabodily and is employed to tactile sense a body location to be treated. However, it will be appreciated that the instruments of the present invention may find uses in other extra or intrabody surgical procedures.

While the suturing devices according to the invention will be described and explained herein as being applied in a novel procedure for bladder-neck suspension used for treatment of urinary incontinence (genuine stress urinary incontinence—GSUI) in females, it is also suitable for application in, e.g., sacro-spinous ligament fixation, and for anchoring suture material, even in conventional transabdominal pelvic surgery, where in obese patients exposure is limited and the surgeon has to rely on palpation of pelvic structures.

The procedure is a surgical treatment of genuine stress urinary incontinence (GSUI) in females, and aims at the correction of the suspension of the anatomical area defined as the "bladder neck", i.e., returning the bladder neck to its former, normal position. Such procedures are known, the one having the highest success rate being the Burch Colposuspension, in which the pelvic fascia and vaginal wall lateral to the urethra is suspended to Cooper's ligament. While this procedure indeed appears to be the most promising, it still is a transabdominal method, requiring general anesthesia, an extensive abdominal incision and hospitalization.

While the procedure facilitated by the present invention follows the same anatomical principles as the above-mentioned Burch method, it is, in contradistinction thereto, a transvaginal, rather than a transabdominal, bilateral suspension of the bladder neck to Cooper's ligament. It is this distinction which turns the treatment, as a matter of fact, into an office, outpatient procedure.

The anchor implanting device described herein can be employed, for example, in an orthopedic procedure known as open Bankart shoulder stabilization.

Recurrent shoulder dislocations are relatively common. In an Israeli epidemiological study (Milgrom et al., Journal of Shoulder and Elbow, November 1998) it was found that 0.05% of soldiers between the ages of 17 and 33 suffer from this problem. The more a population is exposed to trauma or sports the higher the likelihood of dislocations. A shoulder dislocation in an elderly person however does not usually result in recurrent dislocations. Traumatic recurrent shoulder dislocation is usually treated by surgery. In the vast majority of cases, the essential lesion causing the recurrent shoulder instability is a tear of the anterior-inferior or anterior-medial labrium from the glenoid rim. This lesion needs to be repaired so that dislocation can be prevented. The procedure is done under general anesthesia, in a beach chair position. Usually three surgeons are required for executing the procedure. One to retract soft tissue, and two to perform the surgery. The advent of bone suture anchors has made the suture of the labrium back to bone simpler. There is however still considerable difficulty in passing the sutures that are attached to the bone suture anchors implanted in the glenoid rim from underneath the labrium to the labrial superior surface in a very tight anatomical space. Because of this small space, performing the twisting motion of the needle to pass it through the tissue in an exact way is difficult. Typical to this repair of the labrium, 1–3 suture anchors are used and therefore 3 sutures have to be passed. The entrance of the suture at the proper site is very important because the labrium must be returned to its precise anatomical position to ensure a proper repair that will prevent recurrent dislocations. This task is readily performed using the finger-guided anchor implant device of the present invention. It also allows the surgery to be conformably performed with a team of only two surgeons.

The sampling device according to the present invention can be employed as a scalp pH device.

Part of the contemporary management of labor includes evaluation of the fetal well being. This is done by fetal heart monitoring and measurement of fetal blood pH and gases. Fetal heart monitoring is performed by recording the electrical activity of the fetal heart and displaying it as a graph of the fetal heart rate at any time. The fetal blood gases and pH are measured by sampling the fetal blood through the open cervix. The procedure is performed in order to confirm a suspicions of fetal distress that will jeopardize the fetal well being unless treated immediately by delivery of the fetus. Presently, fetal scalp blood sampling can be performed only if the membranes has rapture and the cervix is open enough to allow the introduction of a cone shaped plastic tube with a diameter of 3–4 cm through the vagina and into the cervix. The tube is applied to the fetal scalp in direct contact. The obstetrician scratches the scalp skin using a sharp object through the tube and collects the drop of blood at the site of the scratch. The blood is taken for analysis.

The sampling device of the present invention allows the obstetrician to perform the same procedure in an easier and patient friendly fashion using his finger only. The device will eliminate the need to place the patient in dorsolithotomy position and suffer the discomfort of the large tube applied into her vagina. Mounting a small device that performs blood sampling over the obstetrician's finger enables to sample fetal scalp blood in an earlier stage of labor, in which the cervix opening is smaller, because the obstetricians finger diameter is smaller than the tube diameter.

In cases of Rectal Prolapse, which is a known complication of Cystic Fibrosis, the surgical correction can be perform by constriction of the anal opening which might cause chronic defecation dysfunction or through an abdominal approach. In the transabdominal procedure the upper part of the rectum is anchored to the Sacral bone. Using any of the suturing devices of the present invention can render the anchoring procedure in the small and deep pelvic area an easier and shorter process, avoiding the need of extensive dissection to expose the correct anatomical target.

Another procedure that will benefit from the use of the suturing devices of the present invention is in the case of treating Esophageal reflux in children. The surgical correction is based on reconstruction of a one way valve mechanism around the Esophagus. Passing a "Vessel loop", i.e., a thin rubber band, around the Esophagus prevents the reflux. Any of the suturing devices of the present invention can replace the need for dissection of the Esophagus and makes it easy to pass the Vessel loop behind the esophagus in a short and safe fashion.

Normal vaginal delivery expose the female pelvic floor to muscle and connective tissue trauma which is some cases results in pelvic floor relaxation and pelvic organ prolapse. Vaginal prolapse is a result of weakening of connective tissue support to the vaginal vault apex. One of the most common surgical techniques used to correct vaginal prolapse includes tying the upper part of the vagina to a connective tissue condensation stretched from both side of the sacrum. This anatomical structure is called The Sacrospinous Ligament, and the procedure is called Sacrospinous Ligament Fixation. In order to perform the procedure, the surgeon needs to open the posterior wall of the vagina and enter to a space beside the rectum to reach the ligament. A surgical thread is anchored to the ligament and is thereafter tied to the vagina, thus fixing the upper part of the vagina to the ligament. Since the location of the ligament is deep in the pelvic hole, the surgeon needs to perform extensive dissection to expose the ligament and place the suture material under direct visualization using long instruments. However, palpation of the ligament is easy and within reach of the surgeon's finger. Mounting any of the suturing devices according to the present invention over the surgeon's finger thus enables the surgeon to place the suture in the correct location, avoiding the need for extensive dissection, reduce blood lose and shorten operation time. Palpation of the correct location makes the procedure even safer by reducing the risk of injury to pelvic blood vessels behind certain areas of the ligament.

Rupture of the rectum in large animals, especially horses and cows, oftentimes happens during rectal examination when a peristaltic wave passes over the wrist of the examiner, or following insertion of a stallion's penis into the rectum. Usually a colostomy is done to bypass the rectum and then an attempt is made to suture the tear in the rectum at a distance of 30 to 40 cm from the anus. The suture is placed blindly by palpation of the tear and an attempt is made to place a suture using a needle held by the finger of the operator. Any of the suturing devices according the present invention can be employed to assist suturing the tear.

Injury to the cervix after foaling is a known complication. This leads to infertility because of loss of the fetus through the cervix 1 to 3 months after conception. The present treatment involves placement of sutures into the cervix after conception, so as to reduce the size of the opening. These sutures are inserted blindly by a needle held by the fingers. Any of the suturing devices according to the present invention can be used instead.

In cases of rupture of the uterus at parturition, often the tear is large and repair must be done by means of a laparotomy. However, small tears can be caused by the foot of the foal. Present treatment is effected by placing sutures in the uterus after parturition, to close the small openings and prevent rapture of the uterus in the next pregnancy. Presently, these sutures are placed blindly by a needle held by the fingers. Any of the suturing devices according to the present invention can be used instead.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A finger-guided surgical instrument, comprising:
   (a) a thimble-like element being adapted to surround at least a portion of a surgeon's finger while at least partially exposing the ventral tactile portions of the distal phalanx thereof, so as to enable the surgeon to tactile sense a body location to be treated;
   (b) an ejectable surgical tool being engaged within a housing being formed within, or connected to, a wall of said thimble-like element; and
   (c) a mechanism for ejecting said surgical tool from said thimble-like element, so as to enable the surgeon to operate said body location, said mechanism including a first portion engaged within said housing and which is in contact with said ejectable surgical tool, a second, remote, portion being adapted to extend out of the patient's body and a flexible cable in a tube connecting said first portion to said second portion, said second remote portion being operable by a free hand of the surgeon so as to eject said surgical tool from said thimble-like element.

2. The finger-guided surgical instrument of claim 1, further comprising an adapter insertable between said thimble-like element and the surgeon's finger, so as to adapt the guided surgical instrument to fingers of different size.

3. The finger-guided surgical instrument of claim 1, wherein said mechanism further serves for withdrawing said ejectable surgical tool back into said housing.

4. The finger-guided surgical instrument of claim 1, wherein said wall is a side wall of said thimble-like element.

5. The finger-guided surgical instrument of claim 1, wherein said wall is a front wall of said thimble-like element.

6. The finger-guided surgical instrument of claim 1, wherein said thimble-like element is constructed so as to be mounted over a dorsal side of the distal phalanx of the surgeon's finger, thereby exposing the entire ventral tactile portions of the distal phalanx.

7. The finger-guided surgical instrument of claim 1, wherein said thimble-like element is constructed so as to fully surround the distal phalanx and expose the tip of the ventral tactile portion of the distal phalanx.

8. The finger-guided surgical instrument of claim 1, wherein said thimble-like element is constructed so as to be mounted over a ventral side of the distal phalanx of the surgeon's finger and expose the tip of the ventral tactile portion of the distal phalanx.

9. The finger-guided surgical instrument of claim 1, wherein said surgical tool is ejectable in a direction generally in extension of a longitudinal axis of said thimble-like element.

10. The finger-guided surgical instrument of claim 1, wherein said surgical tool is ejectable in a circular path.

11. The finger-guided surgical instrument of claim 10, wherein said circular path on a plane which substantially parallels a plane traversing the surgeon's finger from top to bottom.

12. The finger-guided surgical instrument of claim 10, wherein said circular path on a plane which substantially parallels a plane traversing the surgeon's finger from side to side.

13. The finger-guided surgical instrument of claim 10, wherein said circular path on a plane which is substantially perpendicular to the longitudinal axis of the surgeon's finger.

14. The finger-guided surgical instrument of claim 1, wherein said surgical tool is selected from the group consisting of a surgical needle, a needle carrying a surgical anchor ejectable therefrom, a puncturing device, an injection needle, a capillary, a puncturing capillary, a miniaturized surgical grasper, miniaturized surgical scissors, a miniaturized blade and an aspiration capillary.

15. The finger-guided surgical instrument of claim 1, further comprising a reporting mechanism for reporting at least one situation selected from the group consisting of a full ejection of said surgical tool, a full withdrawal of said surgical tool, a degree of ejection of said surgical tool and a degree of withdrawal of said surgical tool.

16. The finger-guided surgical instrument of claim 1, further comprising an optical head engaged by said thimble like element.

17. A finger-guided surgical instrument, comprising:

(a) a thimble-like element being adapted to surround at least a portion of a surgeon's finger while at least partially exposing the ventral tactile portions of the distal phalanx thereof, so as to enable the surgeon to tactile sense a body location to be treated;

(b) an ejectable surgical tool being engaged within a housing being formed within, or connected to, a rigid wall of said thimble-like element; and (c) a mechanism for ejecting said surgical tool from said thimble-like element, so as to enable the surgeon to operate said body location, said mechanism including a ratchet member being disposed between said thimble-like element and the surgeon's finger so as to eject said surgical tool from said thimble-like element by twisting back and forth the surgeon's finger.

* * * * *